(12) United States Patent
Kobayashi et al.

(10) Patent No.: US 7,776,868 B2
(45) Date of Patent: Aug. 17, 2010

(54) SUBSTITUTED BICYCLIC AND TRICYCLIC THIENO[2,3-D]PYRIMIDINES AS $A_{2A}$ ADENOSINE RECEPTOR ANTAGONISTS

(75) Inventors: Tetsuya Kobayashi, Sunnyvale, CA (US); Rao Kalla, Sunnyvale, CA (US); Elfatih Elzein, Fremont, CA (US); Jeff Zablocki, San Mateo, CA (US); Brent Blackburn, Los Altos, CA (US)

(73) Assignee: Gilead Palo Alto, Inc., Foster City, CA (US)

( * ) Notice: Subject to any disclaimer, the term of this patent is extended or adjusted under 35 U.S.C. 154(b) by 143 days.

(21) Appl. No.: 11/947,690

(22) Filed: Nov. 29, 2007

(65) Prior Publication Data

US 2008/0188495 A1 Aug. 7, 2008

Related U.S. Application Data

(60) Provisional application No. 60/872,254, filed on Dec. 1, 2006.

(51) Int. Cl.
| | |
|---|---|
| C07D 495/04 | (2006.01) |
| A61K 31/519 | (2006.01) |
| A61P 25/28 | (2006.01) |
| A61P 25/24 | (2006.01) |
| A61P 3/04 | (2006.01) |
| A61P 37/02 | (2006.01) |

(52) U.S. Cl. .................................. 514/260.1; 544/278
(58) Field of Classification Search ................. 544/278; 514/260.1

See application file for complete search history.

(56) References Cited

U.S. PATENT DOCUMENTS

| 3,845,770 | A | 11/1974 | Theeuwes et al. |
|---|---|---|---|
| 4,326,525 | A | 4/1982 | Swanson et al. |
| 4,902,514 | A | 2/1990 | Barclay et al. |
| 5,616,345 | A | 4/1997 | Georghegan et al. |
| 2003/0004172 | A1 | 1/2003 | Harter et al. |
| 2007/0208040 | A1 | 9/2007 | Elzein et al. |

OTHER PUBLICATIONS

Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Vippagunta et al, "Crystalline Solids" Advanced Drug Delivery Reviews, vol. 48, pp. 3-26 (2001).*
Gavezzotti, "Are Crystal Structures Predicatable?" Acc. Chem. Res., vol. 27, pp. 309-314 (1994).*
G. L. Stiles, K. A. Jacobson, and M. F. Jarvis, Wiley-Liss: New York, (1997); pp. 29-37.
V. Ralevic; G. Burnstock, G. Pharmacol. Rev. (1998) vol. 50, 413-492.
Feoktistov et al., Adenosine $A_{2B}$ Receptors as Therapeutic Targets, Drug Dev Res 45:198-206, 1998.
Feoktistov et al., Trends Pharmacol Sci 19:148-153, 1998.
"The Critical Role of Adenosine $A_{2A}$ Receptors and Gi βγ Subunits in Alcoholism and Addiction: From Cell Biology to Behavior", by Ivan Diamond and Lina Yao; (The Cell Biology of Addiction, 2006, pp. 291-316).
"Adaptations in Adenosine Signaling in Drug Dependence: Therapeutic Implications", by Stephen P. Hack and Macdonald J. Christie, Critical Review in Neurobiology, vol. 15, 235-274 (2003).
Rasmusson et al, Ann. NY Acad. Sci.,—821, 332-351, (1997).
Jones et al., Psychopharmacology (Berl), May 2002; 161(3):314-23.
Imaizumi et al., Jpn. J. Psychopharmacol., 15, 125-133 (1995) (abstract).
Bourin et al., Pol. J. Pharmacol., 49, 79-84 (1997) (abstract).
Kantor et al, Physiol. Behav., 71, 551-557 (2000).
Millan et al., Eur. J. Pharmacol., 463, 67-96 (2003).
Takeda et al, Eur. J. Pharmacol., 350, .21-29 (1998).
Ichimaru et al., Jpn. J. Pharmacol. 68, 65-70 (1995).
Mandhane et al, European Journal of Pharmacology, 328 (1997) 135-141.
Vu et al., Journal of Medicinal Chemistry, Aug. 12, 2004;47(17):4291-9.

* cited by examiner

Primary Examiner—Susanna Moore
(74) Attorney, Agent, or Firm—J. Elin Hartrum

(57) ABSTRACT

The present invention relates to novel compounds that are $A_{2A}$ adenosine receptor antagonists having the structure of Formula I

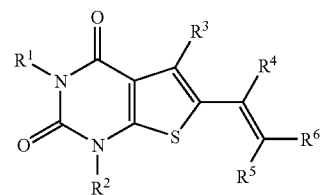

and to their use in treating mammals for various disease states, such as obesity, CNS disorders, including the "movement disorders" (Parkinson's disease, Huntington's Chorea, and catelepsy), and cerebral ischemia, excitotoxicity, cognitive and physiological disorders, depression, ADHD, and drug addiction (alcohol, amphetamine, cannabinoids, cocaine, nicotine, and opioids) and to their use in the enhancement of immune response. The invention also relates to methods for the preparation of such compounds, and to pharmaceutical compositions containing them.

13 Claims, No Drawings

SUBSTITUTED BICYCLIC AND TRICYCLIC THIENO[2,3-D]PYRIMIDINES AS $A_{2A}$ ADENOSINE RECEPTOR ANTAGONISTS

This application claims priority to U.S. Provisional Patent Application Ser. No. 60/872,254, filed Dec. 1, 2006, the entirety of which is incorporated herein by reference.

FIELD OF THE INVENTION

The present invention relates to novel compounds that are $A_{2A}$ adenosine receptor antagonists, and to their use in treating mammals for various disease states, such as obesity, CNS disorders, including the "movement disorders" (Parkinson's disease, Huntington's Chorea, and catalepsy), cerebral ischemia, excitotoxicity, cognitive and physiological disorders, depression, ADHD, hepatic fibrosis, cirrhosis of the liver, and drug addiction (alcohol, amphetamine, cannabinoids, cocaine, nicotine, and opioids), and to their use in enhancing immune response. The invention also relates to methods for the preparation of such compounds, and to pharmaceutical compositions containing them.

BACKGROUND

The effects of adenosine are transduced through adenosine receptors, which are subdivided into four general subtypes; $A_1$, $A_{2A}$, $A_{2B}$, and $A_3$, all of which modulate important physiological processes ((G. L. Stiles, K. A. Jacobson, and M. F. Jarvis, Wiley-Liss: New York, (1997); pp 29-37; V. Ralevic; G. Burnstock, G. *Pharmacol. Rev.* (1998) Vol. 50, 413-492). For example, stimulation of the $A_1$ adenosine receptors shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter. Stimulation of cell surface $A_{2A}$ receptors produces dilation of the coronary resistance vessels, which phenomenon is useful for pharmacological stress imaging. $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, *Drug Dev Res* 45:198; Feoktistov et al., *Trends Pharmacol Sci* 19:148-153). $A_3$ adenosine receptors modulate cell proliferation processes. In particular, compounds that are $A_3$ receptor agonists have utility in the therapeutic and/or prophylactic treatment of cancer, cardiac disease, infertility, kidney disease, and CNS disorders.

Adenosine is an important endogenous purine neuromodulator in the central nervous system. Recently, $A_{2A}$ receptors have been demonstrated to be abundant in the basal ganglia, a region of the brain that is known to be important in motor function. It has been shown that administration of haloperidol or MPTP (N-methyl-4-phenyl-1,2,5,6-tetrahydropyridine) produces symptoms similar to Parkinson's disease in test animals, and these symptoms can be reversed by administration of an $A_{2A}$ receptor antagonist (see, for example, "piperazine Derivatives of [1,2,4] Triazolo[1,5-a][1,3,5]triazine as Potent and Selective Adenosine $A_{2A}$ Receptor Antagonists", by Chi B. Vu et al., Journal of Medicinal Chemistry, 2004).

$A_{2A}$ receptor antagonists also possess neuroprotective properties. $A_{2A}$ antagonists have been shown to block kainate-induced excitotoxicity in the hippocampus, to reduce ischemia-evoked glutamate and aspartate release from the cortex, and to reduce the extent of the ischemia-induced injury in rats and gerbils. Further evidence for $A_{2A}$ receptor mediated neuroprotection arises from studies demonstrating that both cerebral infarct size and neurological deficits following transient ischemia are attenuated in $A_{2A}$ receptor knockout mice.

Stimulation of $A_{2A}$ adenosine receptors produces dilation of the coronary resistance vessels. Although this phenomenon is useful for pharmacological stress imaging, it is not favorable for patients who have elevated endogenous adenosine, because excessive vasodilation potentially leads to coronary steal. The phenomenon of coronary steal can cause tissue damage, because ischemia may be produced in the vascular beds fed by the artery that has lowered blood flow due to the more favorable vasodilation of healthy adjoining arteries. Accordingly, an $A_{2A}$ antagonist will prevent the phenomenon of coronary steal.

It has been shown that adenosine signaling is implicated in drug addiction. All major drugs of abuse (opiates, cocaine, ethanol, and the like) either directly or indirectly modulate dopamine signaling in neurons, in particular those found in the nucleus accumbens, which contains high levels of $A_{2A}$ adenosine receptors. Dependence on addictive substances has been shown to be augmented by the adenosine signaling pathway, and it has been shown that administration of an $A_{2A}$ adenosine receptor antagonist reduces the craving for addictive substances (see, for example, "The Critical Role of Adenosine $A_{2A}$ Receptors and Gi βγ Subunits in Alcoholism and Addiction: From Cell Biology to Behavior", by Ivan Diamond and Lina Yao, (The Cell Biology of Addiction, 2006, pp 291-316), and "Adaptations in Adenosine Signaling in Drug Dependence: Therapeutic Implications", by Stephen P. Hack and Macdonald J. Christie, Critical Review in Neurobiology, Vol. 15, 235-274 (2003)).

It has also been demonstrated that adenosine receptors, in particular the $A_{2A}$ adenosine receptor, play a role in down regulation of inflammation in vivo (see U.S. Patent Application Publication No. 2005/0220799) by acting as a termination mechanism that limits the immune response, and consequently protect normal tissues from excess immune damage during pathogenesis of various diseases. Accordingly, inhibition of signaling through the $A_{2A}$ adenosine receptor intensifies and prolongs the immune response in a mammal, and thus, for example, increases the efficacy of a vaccine when an $A_{2A}$ adenosine antagonist is co-administered with a vaccine.

Accordingly, it is desired to provide compounds that are potent $A_{2A}$ antagonists, useful in the treatment of various disease states related to modulation of the $A_{2A}$ receptor, in particular cardiovascular diseases such as tissue damage caused by ischemia, CNS-related diseases such as Parkinson's disease, the treatment of drug addiction, and improved immunization. Preferably, the compounds would be selective for the $A_{2A}$ receptor, thus avoiding side effects caused by interaction with other adenosine receptors.

SUMMARY OF THE INVENTION

It is an object of this invention to provide $A_{2A}$ receptor antagonists. Accordingly, in a first aspect, the invention relates to compounds of Formula I:

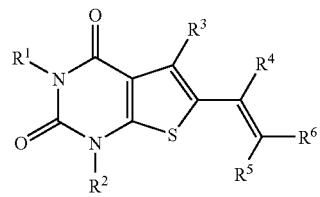

wherein
$R^1$ is hydrogen, optionally substituted $C_{1-6}$ alkyl, optionally substituted $C_{2-10}$ alkenyl, or optionally substituted $C_{2-6}$ alkynyl;

R² is hydrogen, optionally substituted $C_{1-4}$ alkyl, —X—O—P(O)(OR)₂, or —X—O—R⁷, in which X is $C_{1-4}$ alkylene, R is hydrogen or $C_{1-6}$ alkyl, and R⁷ is acyl;

R³ is hydrogen, optionally substituted $C_{1-4}$ alkyl, or a 5 or 6 membered optionally substituted monocyclic heterocycle containing 1, 2, 3, or 4 heteroatoms independently selected from oxygen, sulfur and nitrogen;

R⁴ and R⁵ are independently methyl or hydrogen; and

R⁶ is optionally substituted phenyl, optionally substituted heteroaryl, optionally substituted heterocycle, or optionally substituted cycloalkyl.

In yet another embodiment of the invention, pharmaceutical formulations are provided, comprising a therapeutically effective amount of an $A_{2A}$ receptor antagonist of Formula I, and at least one pharmaceutically acceptable carrier. The formulation is preferably for oral administration.

In a third embodiment of the invention, methods of using the compounds of Formula I in the treatment of a disease or condition in a mammal that can be treated with an $A_{2A}$ receptor antagonist are provided. The method comprises administering to a mammal in need thereof a therapeutically effective dose of a compound of Formula I. Such diseases include, but are not limited to, Parkinson's disease, Huntington's Chorea, and catalepsy, and cerebral ischemia, excitotoxicity, and cognitive and physiological disorders, including the treatment of drug addiction. The compounds of Formula I are also useful for the inhibition of coronary vasodilation, which treatment prevents coronary steal.

At present, the preferred compounds for use in the invention include, but are not limited to:

6-[(1E)-2-(3,4-dimethoxyphenyl)vinyl]-3-ethyl-1,5-dimethyl-1,3-dihydrothiopheno[2,3-d]pyrimidine-2,4-dione;
6-[(1E)-2-(3,4-dimethoxyphenyl)vinyl]-3-ethyl-5-methyl-1-[(phenylmethoxy)methyl]-1,3-dihydrothiopheno[2,3-d]pyrimidine-2,4-dione;
6-((1E)-2-phenylvinyl)-3-ethyl-5-methyl-1,3-dihydrothiopheno[2,3-d]pyrimidine-2,4-dione;
6-[(1E)-2-(4-fluorophenyl)vinyl]-3-ethyl-5-methyl-1,3-dihydrothiopheno[2,3-d]pyrimidine-2,4-dione;
6-((1E)-2-phenylvinyl)-1,5-dimethyl-3-prop-2-ynyl-1,3-dihydrothiopheno[2,3-d]pyrimidine-2,4-dione;
6-[(1E)-2-(3-fluorophenyl)vinyl]-3-ethyl-5-methyl-1,3-dihydrothiopheno[2,3-d]pyrimidine-2,4-dione;
6-[(1E)-2-(4-chlorophenyl)vinyl]-3-ethyl-5-methyl-1,3-dihydrothiopheno[2,3-d]pyrimidine-2,4-dione;
6-[(1E)-2-(4-phenylphenyl)vinyl]-3-ethyl-5-methyl-1,3-dihydrothiopheno[2,3-d]pyrimidine-2,4-dione
6-{(1E)-2-[4-(trifluoromethyl)phenyl]vinyl}-3-ethyl-5-methyl-1,3-dihydrothiopheno[2,3-d]pyrimidine-2,4-dione;
6-((1E)-2-phenylvinyl)-3-ethyl-1,5-dimethyl-1,3-dihydrothiopheno[2,3-d]pyrimidine-2,4-dione;
6-((1E)-2-phenylvinyl)-1,3-diethyl-5-methyl-1,3-dihydrothiopheno[2,3-d]pyrimidine-2,4-dione;
6-((1E)-2-phenylvinyl)-3-ethyl-1-(2-hydroxyethyl)-5-methyl-1,3-dihydrothiopheno[2,3-d]pyrimidine-2,4-dione;
6-[(1E)-2-(3,4-dimethoxyphenyl)vinyl]-3-ethyl-5-methyl-1,3-dihydrothiopheno[2,3-d]pyrimidine-2,4-dione;
6-((1E)-2-phenylvinyl)-5-methyl-3-(2-methylpropyl)-1,3-dihydrothiopheno[2,3-d]pyrimidine-2,4-dione;
6-((1E)-2-phenylvinyl)-3-ethyl-1-(3-hydroxypropyl)-5-methyl-1,3-dihydrothiopheno[2,3-d]pyrimidine-2,4-dione;
6-((1Z)-2-phenylvinyl)-3-ethyl-1-(2-hydroxyethyl)-5-methyl-1,3-dihydrothiopheno[2,3-d]pyrimidine-2,4-dione;
6-[(1E)-2-(3,4-dimethoxyphenyl)vinyl]-5-methyl-3-(2-methylpropyl)-1,3-dihydrothiopheno[2,3-d]pyrimidine-2,4-dione;
6-((1E)-2-(3-pyridyl)vinyl)-3-ethyl-5-methyl-1,3-dihydrothiopheno[2,3-d]pyrimidine-2,4-dione;
6-[(1E)-2-(4-methylphenyl)vinyl]-3-ethyl-5-methyl-1,3-dihydrothiopheno[2,3-d]pyrimidine-2,4-dione;
6-[(1E)-2-(4-methoxyphenyl)vinyl]-3-ethyl-5-methyl-1,3-dihydrothiopheno[2,3-d]pyrimidine-2,4-dione;
6-[(1E)-2-(2-fluorophenyl)vinyl]-3-ethyl-5-methyl-1,3-dihydrothiopheno[2,3-d]pyrimidine-2,4-dione;
6-[(1E)-2-(3-methoxyphenyl)vinyl]-3-ethyl-5-methyl-1,3-dihydrothiopheno[2,3-d]pyrimidine-2,4-dione;
6-[(1E)-2-(2-methoxyphenyl)vinyl]-3-ethyl-5-methyl-1,3-dihydrothiopheno[2,3-d]pyrimidine-2,4-dione;
{6-[(1E)-2-(3,4-dimethoxyphenyl)vinyl]-3-ethyl-5-methyl-2,4-dioxo-1,3-dihydrothiopheno[2,3-d]pyrimidinyl}methyl butanoate; and
6-[(1E)-2-(3,5-dimethoxyphenyl)vinyl]-3-ethyl-5-methyl-1,3-dihydrothiopheno[2,3-d]pyrimidine-2,4-dione.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO—aryl, —SO-heteroaryl, —SO₂-alkyl, SO₂-aryl and —SO₂-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2; or 2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "substituted alkylene" refers to:

(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3, 3-trimethylbicyclo[2.2.1]hept-2-yl, (2,3,3-trimethylbicyclo [2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives.

Unless otherwise constrained by the definition for the heteroaryl or heteroarylene substituent, such heteroaryl or heteroarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—.

The term "thiocarbonyl" refers to a group —C(S)—.

The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I and Formula II" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoiscmers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

"Topical administration" shall be defined as the delivery of the therapeutic agent to the surface of the wound and adjacent epithelium.

"Parenteral administration" is the systemic delivery of the therapeutic agent via injection to the patient.

The term "therapeutically effective amount" refers to that amount of a compound of Formula I that is sufficient to effect treatment, as defined below, when administered to a mammal in need of such treatment. The therapeutically effective amount will vary depending upon the specific activity of the therapeutic agent being used, and the age, physical condition, existence of other disease states, and nutritional status of the patient. Additionally, other medication the patient may be receiving will effect the determination of the therapeutically effective amount of the therapeutic agent to administer.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "opioids" as used herein includes morphine, codeine, heroin, oxycodone (OxyContin), propoxyphene (Darvon), hydrocodone (Vicodin), and hydromorphone (Dilaudid), as well as meperidine (Demerol).

The term "excitotoxicity" means a pathological process by which nerve cells are damaged and killed by glutamate and similar substances. Excitotoxicity may be involved in stroke, traumatic brain injury and neurodegenerative diseases of the central nervous system (CNS) such as multiple sclerosis, Alzheimer's disease, Amyotrophic lateral sclerosis (ALS), Parkinson's disease and Huntington's disease.

Nomenclature

The naming and numbering of the compounds of the invention is illustrated with a representative compound of Formula I in which $R^2$ and $R^3$ are methyl, $R^1$ is ethyl, $R^4$ and $R^5$ are hydrogen, and $R^6$ is 3,4-dimethoxyphenyl,

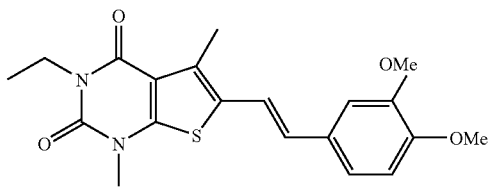

which is named:

6-[(1E)-2-(3,4-dimethoxyphenyl)vinyl]-3-ethyl-1,5-dimethyl-1,3-dihydrothiopheno[2,3-d]pyrimidine-2,4-dione.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I

One method of preparing compounds of Formula I is shown in Reaction Scheme I.

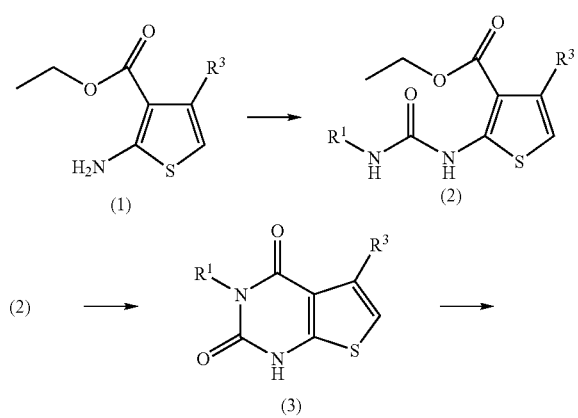

REACTION SCHEME I

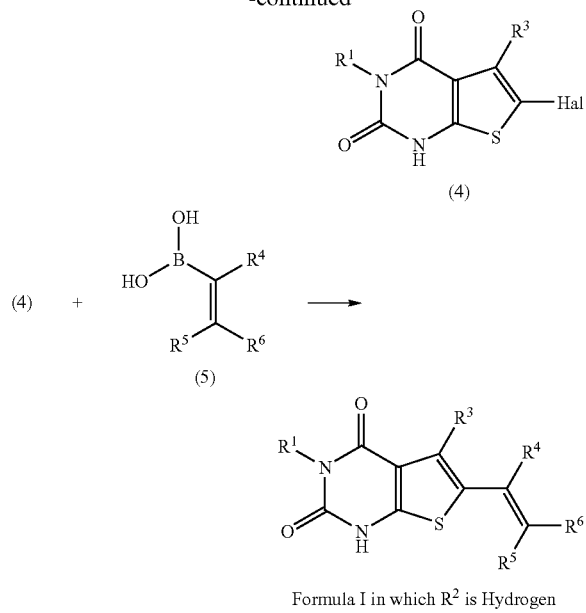

Step 1—Preparation of a Compound of Formula (2)

The compound of formula (1) is commercially available. Initially, a carboxylic acid of formula $R^1CO_2H$ is reacted with diphenylphosphoryl azide and a base, and the resulting mixture reacted with a compound of formula (1) to provide a compound of formula (2). In general, the carboxylic acid is dissolved in an inert solvent, for example benzene or toluene, and diphenylphosphoryl azide and a tertiary organic base added, for example triethylamine, and the mixture stirred at reflux for about 1 hour. The compound of formula (1) is then added and the mixture refluxed for about 10-24 hours. When the reaction is substantially complete, the product of formula (2) is isolated by conventional means, for example by partitioning between ethyl acetate and water and purifying the product, for example by chromatography or recrystallization.

It should be noted that reaction of (1) with a carboxylic acid of formula $R^1CO_2H$ in the presence of diphenylphosphoryl azide and a base is in effect reaction of (1) with an isocyanate of the formula $R^1NCO$. Many isocyanates are commercially available, or may be prepared by means well known in the art, and can be used directly in the above reaction in place of a mixture of $R^1CO_2H$, diphenylphosphoryl azide and a base.

Step 2—Preparation of a Compound of Formula (3)

The compound of formula (2) is cyclized to a compound of formula (3) by reaction with an alkoxide in a protic solvent, for example sodium ethoxide in ethanol. The reaction is conducted at about room temperature for about 1-8 hours. When the reaction is substantially complete, the product of formula (3) is isolated and purified by conventional means.

Step 4—Preparation of a Compound of Formula (4)

The compound of formula (3) is reacted with a halogenating agent such as a brominating or iodoinating reagent, for example N-bromosuccinimide or N-iodosuccinimide. In general, the compound of formula (3) is dissolved in an inert solvent, for example chloroform, and cooled to about 0° C. The halogenating agent is then added, and the two compounds are stirred until the reaction is complete, for example about 5-60 minutes. When the reaction is substantially complete, the product of formula (4) is isolated and purified by conventional means, for example by partitioning between methylene chloride and water. Removal of the solvent provides a compound of formula (4).

Step 5—Preparation of a Compound of Formula I

When a brominating agent is used in Step 4, the compound of formula (4) is reacted with a compound of the formula (5), which is commercially available or prepared by means well known in the art, in the presence of a catalytic amount of tetrakis(triphenylphosphine)palladium. In general, the compound of formula (4) is dissolved in an inert solvent, for example dimethoxyethane, and the compound of formula (5) added, followed by the palladium catalyst and aqueous sodium carbonate solution. The reaction is conducted at a temperature of about reflux, for about 8-24 hours. When the reaction is substantially complete, the product of Formula I is isolated and purified by conventional means, for example by partitioning between ethyl acetate and water. Removal of the solvent provides a crude compound of Formula I, which may be further purified by crystallization from an inert solvent, for example ethyl acetate.

When an iodoinating agent is used in Step 4, the compound of formula (4) may be reacted with a vinylstannane compound of the formula (5') as shown below which is commercially available or prepared by means well known in the art.

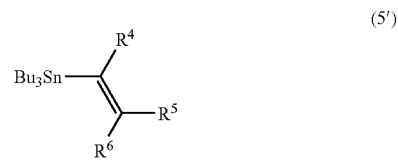

The compound of formulas (4) and (5') are reacted with $Pd(Ph_3P)_4$ in DMF under argon atmosphere at room temperature. The combined reactants are heated by microwave reactor at approximately 140° C. to 160° C. for 5 to 15 min. The product of Formula I is then isolated and purified by conventional means, for example by filtration through Celite followed by washing with EtOAc and brine and then drying with $Na_2SO_4$. After filtering off the drying agent, the solvent may be removed under reduced pressure to give a crude mixture which then maybe purified using a column-chromatography followed by recrystallization.

When desired, compounds of Formula I in where $R^2$ is not hydrogen may be synthesized by subsequent reaction. A method of preparing compounds of Formula I in which $R^2$ is not hydrogen is shown in Reaction Scheme II.

REACTION SCHEME II

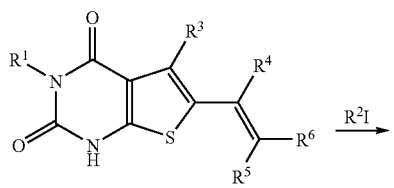

Formula I in which $R^2$ is Hydrogen

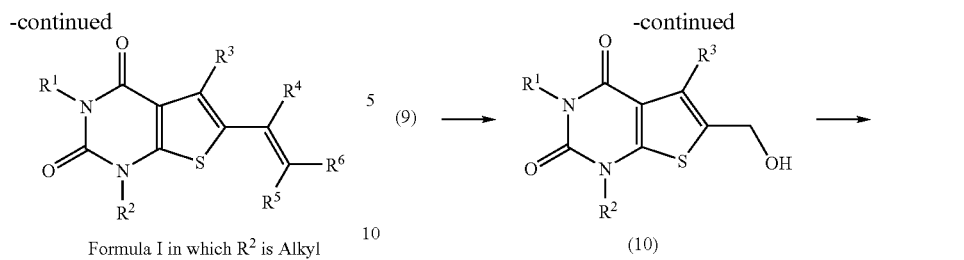

Formula I in which R² is Alkyl

Preparation of a Compound of Formula I in which R² is Other than Hydrogen

The compound of Formula I in which R is hydrogen is reacted with a compound of the formula R²Halo, where Halo is chloro, bromo, or iodo. In general, the compound of Formula I is dissolved in a polar solvent, for example N,N-dimethylformamide, and the compound of formula R²Halo added, followed by a base, for example triethylamine or potassium carbonate. The reaction is conducted at a temperature of about room temperature, for about 8-24 hours. When the reaction is substantially complete, the product of Formula I is isolated and purified by conventional means, for example by removal of the solvent and purifying the residue, for example by chromatography.

An alternative method of preparing the compounds of the invention in which R² is other than hydrogen is shown in Reaction Scheme III.

REACTION SCHEME III

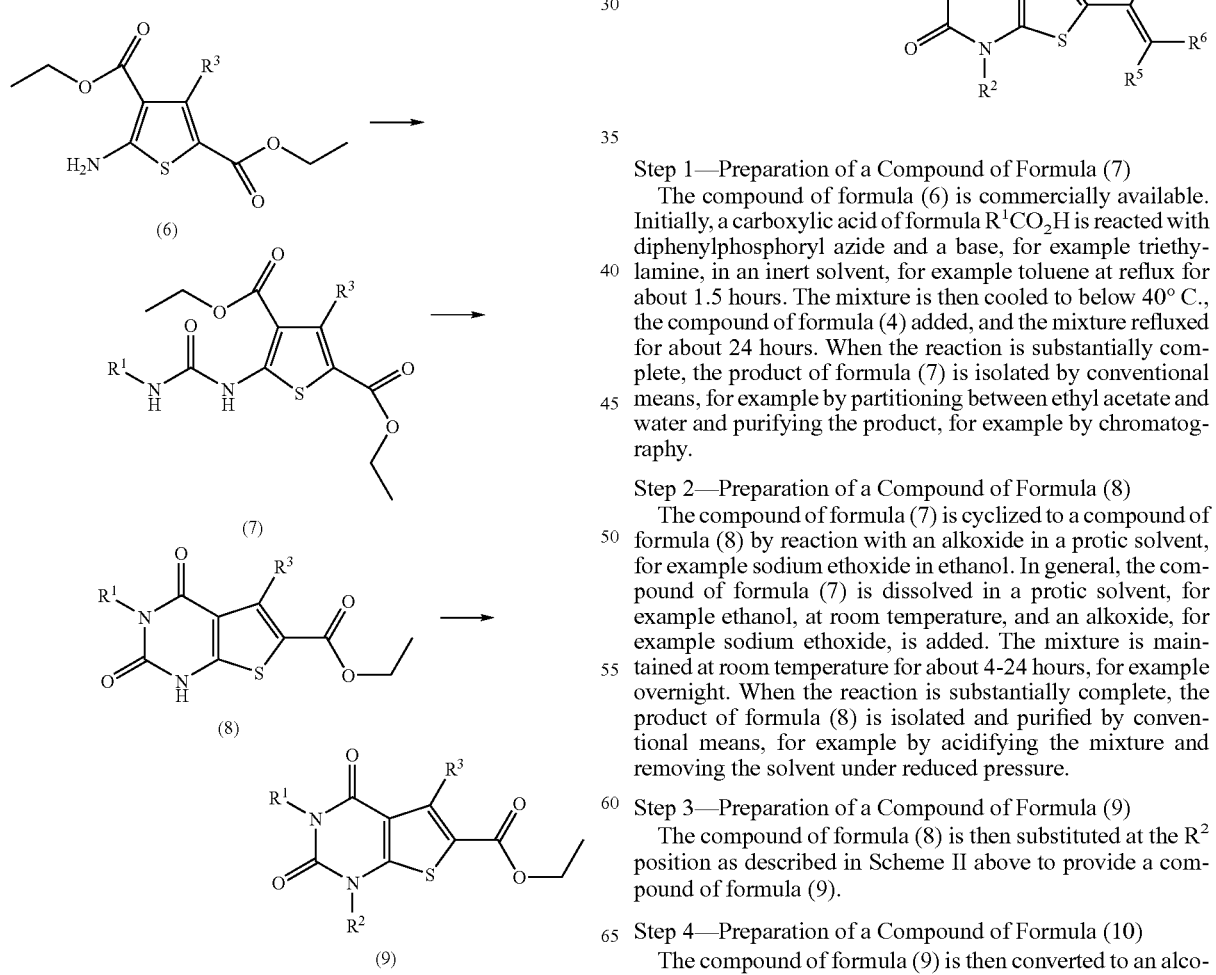

Step 1—Preparation of a Compound of Formula (7)

The compound of formula (6) is commercially available. Initially, a carboxylic acid of formula $R^1CO_2H$ is reacted with diphenylphosphoryl azide and a base, for example triethylamine, in an inert solvent, for example toluene at reflux for about 1.5 hours. The mixture is then cooled to below 40° C., the compound of formula (4) added, and the mixture refluxed for about 24 hours. When the reaction is substantially complete, the product of formula (7) is isolated by conventional means, for example by partitioning between ethyl acetate and water and purifying the product, for example by chromatography.

Step 2—Preparation of a Compound of Formula (8)

The compound of formula (7) is cyclized to a compound of formula (8) by reaction with an alkoxide in a protic solvent, for example sodium ethoxide in ethanol. In general, the compound of formula (7) is dissolved in a protic solvent, for example ethanol, at room temperature, and an alkoxide, for example sodium ethoxide, is added. The mixture is maintained at room temperature for about 4-24 hours, for example overnight. When the reaction is substantially complete, the product of formula (8) is isolated and purified by conventional means, for example by acidifying the mixture and removing the solvent under reduced pressure.

Step 3—Preparation of a Compound of Formula (9)

The compound of formula (8) is then substituted at the R² position as described in Scheme II above to provide a compound of formula (9).

Step 4—Preparation of a Compound of Formula (10)

The compound of formula (9) is then converted to an alcohol by reaction with a reducing agent such as $LiBH_4$ or the like in tetrahydrofuran. The reaction typically takes place under reflux conditions for 1 to 4 hours after which the compound of formula (10) isolated and purified by conventional means, for example by addition of $H_2O$ and MeOH followed by extraction with AcOEt, solvent removal under reduced pressure, and then recrystallization in AcOEt/hexane.

Step 5—Preparation of a Compound of Formula (11)

The alcohol of formula (10) is then modified to provide an aldehyde of formula (11) by reaction with an oxidizing agent such as pyridinium chlorochromate or manganese dioxide in trichloromethane. The resulting aldehyde compound of formula (11) is then isolated using conventional techniques, i.e., solvent removal by evaporation followed by recrystallization in AcOEt. Additional product of formula (11) can be obtained using column-chromatography.

Step 6—Preparation of a Compound of Formula I

The aldehyde of formula (11) is then is then reacted with a diethylmethylphosphonate derivative of formula (12). The two reactants are typically dissolved in THF and then added t-BuOK under nitrogen atmosphere at room temperature. The reaction proceeds at room temperature for 1 to 4 hours until the compound of formula (11) disappears. The compound of Formula I is the collected by addition of water and AcOEt followed by filtration of the resulting biphasic suspension and recrystallization in a DMF/benzene mixture to provide the desired compound of Formula I.

The diethylmethylphosphonate derivative of formula (12) may be synthesized according to conventional procedures. For example, a compound of formula (12) wherein $R^4$ and $R^5$ are hydrogen and $R^6$ is 3,4-dimethoxy phenyl may be produced by the method shown in Reaction Scheme IV.

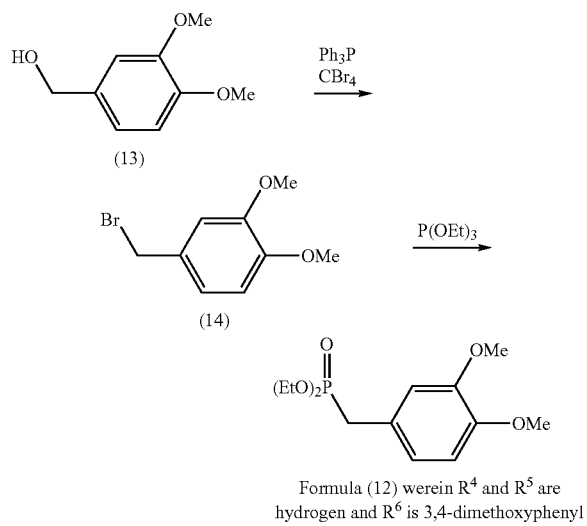

REACTION SCHEME IV

Formula (12) werein $R^4$ and $R^5$ are hydrogen and $R^6$ is 3,4-dimethoxyphenyl Step 1—Preparation of a Compound of Formula (14)

A commercially available alcohol such as the compound of formula (13) may be reacted with $CBr_4$ and $CHCl_3$ under nitrogen atmosphere at room temperature in order to provide the brominated derivative of formula (14). The reaction typically takes place under a nitrogen gas using $PPh_3$ as a catalyst. The compound may be precipitated from solution by the addition of a polar solvent such as hexane and collected by filtration.

Step 2—Preparation of a Compound of Formula (12)

The bromide compound of formula (14) is then reacted with $P(OEt)_3$ at reflux conditions for about 1 hour. After cooling down to ambient temperature, the mixture can be directly loaded onto a column-chromatography to give the phosphonate compound of formula (12).

Utility Testing and Administration

General Utility

The compounds of the invention are $A_{2A}$ adenosine receptor antagonists, and are effective for treating mammals for various disease states, such as CNS disorders, including the "movement disorders" (Parkinson's disease, Huntington's Chorea, and catalepsy), and cerebral ischemia, excitotoxicity, cognitive and physiological disorders, depression, ADHD, and drug addiction (alcohol, amphetamines, cannabinoids, cocaine, nicotine, and opioids).

Testing

Activity testing is conducted as described in those patents and patent applications referenced above, and in the Examples below, and by methods apparent to one skilled in the art.

Utility of the compounds of the invention for the treatment of Parkinson's disease can be tested by reversal of mouse catalepsy. In general, catalepsy is induced in mice by subcutaneous injection of haloperidol, and then the test compound is administered by oral gavage. Reversal of catalepsy demonstrates efficacy in the treatment of Parkinson's disease.

Utility of the compounds of the invention for the treatment of alcoholism can be tested by determining whether such compounds reduce the incidence of self-administration of ethanol in rats.

Utility of the compounds of the invention for the treatment of anxiety can be tested by use of the following published procedures:

Behavioral models in psychopharmacology: theoretical, industrial, and clinical perspectives, Cambridge University Press, p. 21-49 (1991); and Ann. NY Acad. Sci., -821, 332-351, (1997);

The elevated plus maze test is a model of anxiety disorder, especially for GAD, panic disorder, agoraphobia and specific phobia Psychopharmacol., 161, 314-323 (2002); Jpn. J. Psychopharmacol., 15, 125-133 (1995), and Pol. J. Pharmacol., 49, 79-84 (1997);

The social interaction test is a model of anxiety disorder, especially for GAD and social phobia, and is described in Physiol. Behav., 71, 551-557 (2000);

The vogel conflict test is a model of anxiety disorder, especially for GAD, and is described in Eur. J. Pharmacol., 463, 67-96 (2003);

The hole-board test is a model of anxiety disorder, especially for GAD, and is described in Eur. J. Pharmacol., 350, 21-29 (1998), and Pol. J. Pharmacol., 49, 79-84 (1997).

The marble burying test is a model of anxiety disorder, especially for OCD, and is described in Jpn. J. Pharmacol. 68, 65-70 (1995); and Learned helplessness is a model of anxiety disorder, especially for PTSD, and is described in Green et al., Behavioral models in psychopharmacology: theoretical, industrial, and clinical perspectives, Cambridge University Press, p. 21-49 (1991); and Ann. NY Acad. Sci., 821, 332-351, (1997).

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including buccal, intranasal, intra-arterial injection, intravenously, intraperitoneally, parenterally, intramuscularly, subcutaneously, orally, or as an inhalant.

Oral administration is the preferred route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992, 445 and 5,001,139. Such patches may be constructed for continuous, pulsatile, or on demand delivery of pharmaceutical agents.

Adenosine $A_{2A}$ receptor antagonists such as the compounds of Formula I are effective over a wide dosage range and is generally administered in a pharmaceutically effective amount. Typically, for oral administration, each dosage unit contains from 1 mg to 2 g of an adenosine $A_{2A}$ receptor antagonist, more commonly from 1 to 700 mg, and for parenteral administration, from 1 to 700 mg of an adenosine $A_{2A}$ receptor antagonist, more commonly about 2 to 200 mg. It will be understood, however, that the amount of the adenosine $A_{2A}$ receptor antagonist actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of a Compound of Formula (2)

Preparation of a Compound of Formula (2) in which R¹ is Ethyl and R³ is Methyl

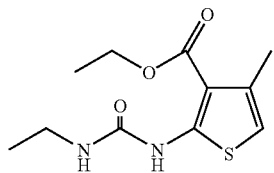

A mixture of propionic acid (3.8 ml, 50.64 mmol), diphenylphosphoryl azide (10.9 ml, 50.64 mmol), and triethylamine (7.1 ml, 50.64 mmol) in toluene (30 ml) was refluxed for 1 hour. After cooling to room temperature, ethyl 2-amino-4-methylthiophene-3-carboxylate (3.13 g, 16.88 mmol) was added, and the mixture was refluxed for 18 hours. The product was partitioned between ethyl acetate and water, the organic layer washed with brine, dried over sodium sulfate, and solvent removed under reduced pressure. The residue was chromatographed on silica gel, eluting with ethyl acetate/hexane 1:1, to provide ethyl 4-methyl-2-[(methylamino)carbonylamino]-thiophene-3-carboxylate as pink crystals.

Preparation of Compounds of Formula (2) Varying R¹ and R³

Similarly, following the procedure of Example 1A above, but optionally substituting other compounds of formula (1) for ethyl 2-amino-4-methylthiophene-3-carboxylate, and optionally substituting other carboxylic acids of formula R¹CO₂H for acetic acid, the following compounds of formula (2) were prepared:

ethyl 4-methyl-2-[(ethylamino)carbonylamino]thiophene-3-carboxylate;
ethyl 4-methyl-2-[(propylamino)carbonylamino]thiophene-3-carboxylate;
ethyl 4-methyl-2-{[(methylethyl)amino]carbonylamino}thiophene-3-carboxylate;
ethyl 4-methyl-2-{[(2-methylpropyl)amino]carbonylamino}thiophene-3-carboxylate;
ethyl 2-[(butylamino)carbonylamino]-4-methylthiophene-3-carboxylate;
ethyl 2-{[(cyclopropylmethyl)amino]carbonylamino}-4-methylthiophene-3-carboxylate;
ethyl 4-methyl-2-[(phenylamino)carbonylamino]thiophene-3-carboxylate;
ethyl 4-methyl-2-[(2-thienylamino)carbonylamino]thiophene-3-carboxylate;
ethyl 4-methyl-2-({[(4-methylphenyl)methyl]amino}carbonylamino)thiophene-3-carboxylate;
ethyl 2-[(ethylamino)carbonylamino]-4-phenylthiophene-3-carboxylate;
ethyl 2-[(ethylamino)carbonylamino]-4-(2-furyl)thiophene-3-carboxylate;
ethyl 2-[(ethylamino)carbonylamino]-4-(2-thienyl)thiophene-3-carboxylate;
ethyl 2-[(ethylamino)carbonylamino]-4-(4-phenylphenyl)thiophene-3-carboxylate; and
ethyl 2-[(ethylamino)carbonylamino]-4-(methylethyl)thiophene-3-carboxylate.

C. Preparation of Compounds of Formula (2) Varying R¹ and R³

Similarly, following the procedure of Example 1A above, but optionally substituting other compounds of formula (1) for ethyl 2-amino-4-methylthiophene-3-carboxylate, and optionally substituting other carboxylic acids of formula R¹CO₂H for acetic acid substituting carboxylic acids of formula R¹CO₂H, where R¹ is as defined above for acetic acid, other compounds of formula (2) are prepared.

Example 2

Preparation of a Compound of Formula (3)

A. Preparation of a Compound of Formula (3) in which R¹ is Ethyl and R³ is Methyl

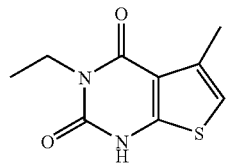

To a suspension of ethyl 4-methyl-2-[(ethylamino)carbonylamino]thiophene-3-carboxylate (3.45 g, 13.46 mmol) in ethanol (10 ml) was added a solution of sodium ethoxide (2M in ethanol, 10 ml, 20 mmol) at room temperature, and the mixture stirred at room temperature for 2 hours. Ice was then added to the reaction mixture, which was then cooled in an ice bath and acidified with concentrated hydrochloric acid to a pH of less than 1. Water (70 ml) was then added, and the resulting solid filtered off, washed with water, and then dried under reduced pressure to provide 3-ethyl-5-methyl-1,3-dihydrothiopheno[2,3-b]pyrimidine-2,4-dione.

B. Preparation of a Compound of Formula (3) Varying R¹ and R³

Similarly, following the procedure of Example 2A above, but substituting other compounds of formula (2) for ethyl 4-methyl-2-[(methylamino)carbonylamino]-thiophene-3-carboxylate, the following compounds of formula (3) were prepared.

3,5-dimethyl-1,3-dihydrothiopheno[2,3-b]pyrimidine-2,4-dione;
3-propyl-5-methyl-1,3-dihydrothiopheno[2,3-b]pyrimidine-2,4-dione;
3-methylethyl-5-methyl-1,3-dihydrothiopheno[2,3-b]pyrimidine-2,4-dione;
3-(2-methylpropyl)-5-methyl-1,3-dihydrothiopheno[2,3-b]pyrimidine-2,4-dione;
3-butyl-5-methyl-1,3-dihydrothiopheno[2,3-b]pyrimidine-2,4-dione;
3-cyclopropylmethyl-5-methyl-1,3-dihydrothiopheno[2,3-b]pyrimidine-2,4-dione;
3-phenyl-5-methyl-1,3-dihydrothiopheno[2,3-b]pyrimidine-2,4-dione;

3-(2-thienyl)-5-methyl-1,3-dihydrothiopheno[2,3-b]pyrimidine-2,4-dione;
3-(4-methylphenyl)-5-methyl-1,3-dihydrothiopheno[2,3-b]pyrimidine-2,4-dione;
3-ethyl-5-(methylethyl)-1,3-dihydrothiopheno[2,3-b]pyrimidine-2,4-dione;
3-ethyl-5-phenyl-1,3-dihydrothiopheno[2,3-b]pyrimidine-2,4-dione;
3-ethyl-5-(4-phenylphenyl)-1,3-dihydrothiopheno[2,3-b]pyrimidine-2,4-dione;
3-ethyl-6-methyl-1,3-dihydrothiopheno[2,3-b]pyrimidine-2,4-dione;
1,5-dimethyl-3-prop-2-ynyl-1,3-dihydrothiopheno[2,3-b]pyrimidine-2,4-dione;
3-ethyl-5-(2-furyl)-1,3-dihydrothiopheno[2,3-b]pyrimidine-2,4-dione; and
3-ethyl-5-(2-thienyl)-1,3-dihydrothiopheno[2,3-b]pyrimidine-2,4-dione.

C. Preparation of Compounds of Formula I in which $R^2$ is Hydrogen

Similarly, following the procedure of Example 2A above, but substituting other compounds of formula (2) for ethyl 4-methyl-2-[(methylamino)carbonylamino]-thiophene-3-carboxylate, other compounds of Formula I in which $R^2$ is hydrogen are prepared.

Example 3

Preparation of a Compound of Formula (4)

A. Preparation of a Compound of Formula (4) in which Hal is Br, $R^1$ is Ethyl and $R^3$ is Methyl

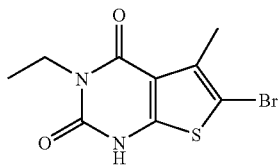

A suspension of 3-ethyl-5-methyl-1,3-dihydrothiopheno[2,3-b]pyrimidine-2,4-dione (2.58 g, 12.27 mmol) in chloroform (60 ml) was cooled to 0° C., and N-bromosuccinimide (2.18 g, 12.27 mmol) added in portions over 15 minutes with stirring. The mixture was stirred for 30 minutes, then methanol (10 ml) was added, causing the solid to go into solution. The solution was extracted with water (30 ml), and the aqueous layer washed with methylene chloride (2×50 ml). After combining the organic layers, a solid formed, and thus a further 20 ml of methanol was added to dissolve the solid. The solution was dried over sodium sulfate, filtered, and the solvent removed from the filtrate under reduced pressure, providing 6-bromo-3-ethyl-5-methyl-1,3-dihydrothiopheno[2,3-b]pyrimidine-2,4-dione as brown crystals. Crystallization of this solid from ethyl acetate (30 ml) provided a light brown solid. Chromatography of the residue on silica gel, eluting with ethyl acetate/hexane 1:1 provided further purified product.

B. Preparation of a Compound of Formula (4), Varying $R^1$ and $R^2$

Similarly, following the procedure of Example 3A above, but substituting other compounds of formula (3) for 3-ethyl-5-methyl-1,3-dihydrothiopheno[2,3-b]pyrimidine-2,4-dione, the following compounds of formula (4) were prepared.
6-bromo-3-ethyl-5-methyl-1,3-dihydrothiopheno[2,3-b]pyrimidine-2,4-dione;
6-bromo-3-propyl-5-methyl-1,3-dihydrothiopheno[2,3-b]pyrimidine-2,4-dione;
6-bromo-3-methylethyl-5-methyl-1,3-dihydrothiopheno[2,3-b]pyrimidine-2,4-dione;
6-bromo-3-(2-methylpropyl)-5-methyl-1,3-dihydrothiopheno[2,3-b]pyrimidine-2,4-dione;
6-bromo-3-butyl-5-methyl-1,3-dihydrothiopheno[2,3-b]pyrimidine-2,4-dione;
6-bromo-3-cyclopropylmethyl-5-methyl-1,3-dihydrothiopheno[2,3-b]pyrimidine-2,4-dione;
6-bromo-3-phenyl-5-methyl-1,3-dihydrothiopheno[2,3-b]pyrimidine-2,4-dione;
6-bromo-3-(2-thienyl)-5-methyl-1,3-dihydrothiopheno[2,3-b]pyrimidine-2,4-dione;
6-bromo-3-(4-methylphenyl)-5-methyl-1,3-dihydrothiopheno[2,3-b]pyrimidine-2,4-dione; and
6-bromo-3-ethyl-5-(methylethyl)-1,3-dihydrothiopheno[2,3-b]pyrimidine-2,4-dione.

C. Preparation of Compounds of Formula (4) Varying $R^1$ and $R^2$

Similarly, following the procedure of Example 3A above, but substituting other compounds of formula (3) for 3-ethyl-5-methyl-1,3-dihydrothiopheno[2,3-b]pyrimidine-2,4-dione, other compounds of formula (4) are prepared, for example:
6-bromo-3-ethyl-5-phenyl-1,3-dihydrothiopheno[2,3-b]pyrimidine-2,4-dione;
6-bromo-3-ethyl-5-(4-phenylphenyl)-1,3-dihydrothiopheno[2,3-b]pyrimidine-2,4-dione;
6-bromo-3-ethyl-5-(2-furyl)-1,3-dihydrothiopheno[2,3-b]pyrimidine-2,4-dione; and
6-bromo-3-ethyl-5-(2-thienyl)-1,3-dihydrothiopheno[2,3-b]pyrimidine-2,4-dione.

Example 4

Preparation of a Compound of Formula I

A. Preparation of a Compound of Formula I in which $R^1$ is Ethyl, $R^2$, $R^4$, and $R^5$ are Hydrogen, $R^3$ is Methyl, and $R^6$ is Phenyl

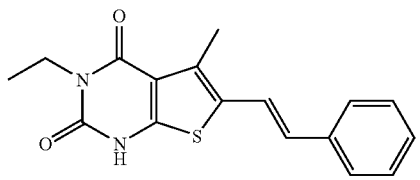

A 3 mL Smith Process Vial was charged with 6-bromo-3-ethylthieno[2,3-b]pyrimidine-2,4-dione (48.8 mg, 0.1688 mmol), 2-phenylethenylboronic acid (70.0 mg, 0.422 mmol, 2.5 equiv) and Pd(Ph$_3$P)$_4$ (9.8 mg, 0.00844 mmol, 0.05 equiv) under argon atmosphere. Into the flask were added DME (2 mL) and 2M-Na$_2$CO$_3$ (0.5 mL) at room temperature so that concentration of the starting material becomes 0.07 M. The mixture was heated by microwave reactor at 160° C. for 10 min. (Emrys Optimizer microwave, Smith Process Vial and Emrys Optimizer are registered trademarks of Personal chemistry, Inc., Uppsala). The mixture was filtered through Celite (3 g) and the Celite was washed with EtOAc (70 mL). The filtrate was washed with brine (30 mL) and dried with $Na_2SO_4$. After filtering off the drying agent, the solvent was removed under reduced pressure to give a crude mixture. Purification by recrystallization of the crude mixture from AcOEt (4 mL) afforded the 3-ethyl-5-methyl-6-(E-2-phenylethenyl}thieno[2,3-b]pyrimidine-2,4-dione as a light brown powder.

$^1$H NMR: (400 MHz, $CDCl_3$).

1.30 (3H, t, J=7.0 Hz, $NCH_2CH_3$), 2.60 (3H, s, C (5) Me), 4.09 (2H, q, J=7.0 Hz, $NCH_2CH_3$), 6.71 (1H, d, J=16.0 Hz, —CH═CH-Ph), 7.25 (1H, d, J=16.0 Hz, —CH═CH-Ph), 7.27 (1H, bd t, J=7.8 Hz, C (4") H), 7.36 (2H, br t, J=7.8 Hz, C (3") H+C (5") H), 7.46 (2H, br d, J=7.8 Hz, C (2") H+C (6") H).

MS (EI): 313 ($M^+$+1), 284, 261, 182.

B. Preparation of a Compound of Formula I, Varying $R^1$, $R^2$, and $R^3$

Similarly, following the procedure of Example 4A above, but optionally substituting other compounds of formula (4) for 6-bromo-3-ethylthieno[2,3-b]pyrimidine-2,4-dione, and optionally substituting other boronic acid derivatives for 2-phenylethenylboronic acid, the following compounds of Formula I were prepared:

6-[(1E)-2-(4-fluorophenyl)vinyl]-3-ethyl-5-methyl-1,3-dihydrothiopheno[2,3-b]pyrimidine-2,4-dione;

6-[(1E)-2-(3-fluorophenyl)vinyl]-3-ethyl-5-methyl-1,3-dihydrothiopheno[2,3-b]pyrimidine-2,4-dione;

6-[(1E)-2-(4-chlorophenyl)vinyl]-3-ethyl-5-methyl-1,3-dihydrothiopheno[2,3-b]pyrimidine-2,4-dione;

6-[(1E)-2-(4-phenylphenyl)vinyl]-3-ethyl-5-methyl-1,3-dihydrothiopheno[2,3-b]pyrimidine-2,4-dione;

6-{(1E)-2-[4-(trifluoromethyl)phenyl]vinyl}-3-ethyl-5-methyl-1,3-dihydrothiopheno[2,3-b]pyrimidine-2,4-dione;

6-[(1E)-2-(3,4-dimethoxyphenyl)vinyl]-3-ethyl-5-methyl-1,3-dihydrothiopheno[2,3-b]pyrimidine-2,4-dione;

6-[(1E)-2-(4-methylphenyl)vinyl]-3-ethyl-5-methyl-1,3-dihydrothiopheno[2,3-b]pyrimidine-2,4-dione;

6-[(1E)-2-(4-methoxyphenyl)vinyl]-3-ethyl-5-methyl-1,3-dihydrothiopheno[2,3-b]pyrimidine-2,4-dione;

6-[(1E)-2-(2-fluorophenyl)vinyl]-3-ethyl-5-methyl-1,3-dihydrothiopheno[2,3-b]pyrimidine-2,4-dione;

6-[(1E)-2-(2-methoxyphenyl)vinyl]-3-ethyl-5-methyl-1,3-dihydrothiopheno[2,3-b]pyrimidine-2,4-dione;

6-[(1E)-2-(3,5-dimethoxyphenyl)vinyl]-3-ethyl-5-methyl-1,3-dihydrothiopheno[2,3-b]pyrimidine-2,4-dione;

6-((1E)-2-phenylvinyl)-5-methyl-3-(2-methylpropyl)-1,3-dihydrothiopheno[2,3-b]pyrimidine-2,4-dione; and 6-[(1E)-2-(3,4-dimethoxyphenyl)vinyl]-5-methyl-3-(2-methylpropyl)-1,3-dihydrothiopheno[2,3-b]pyrimidine-2,4-dione.

C. Preparation of Compounds of Formula I Varying $R^1$, $R^3$, and $R^6$

Similarly, following the procedure of Example 4A above, but optionally substituting other compounds of formula (4) for 6-bromo-3-ethylthieno[2,3-b]pyrimidine-2,4-dione, and optionally substituting other boronic acid derivatives for 2-phenylethenylboronic acid, other compounds of Formula I are prepared.

Example 5

Preparation of a Compound of Formula (4)

A. Preparation of a Compound of Formula (4) in which Hal is I, $R^1$ is Ethyl and $R^3$ is Methyl

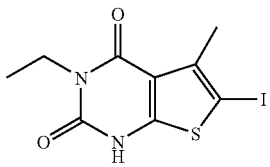

A 100 mL round bottom flask was charged with 3-ethyl-5-methylthieno[2,3-b]pyrimidine-2,4-dione (513.2 mg, 2.44 mmol). Into the flask was added $CHCl_3$ (6 mL) at room temperature to suspend the starting material. To the resulting suspension was added N-iodosuccinimide (549.2 mg, 2.44 mmol, 1.0 equiv) portion-wise over 15 min at 0 degree Celsius. The mixture was stirred for 30 min at same temperature. After the reaction went to completion, MeOH (10 mL) was added into the reaction mixture. Resulting suspension was filtered to collect the first crop as light pink powder (549.0 mg). Obtained mother liquid was concentrated and a recrystallization from EtOAc (4 mL) gave the second crop (179.9 mg) as light yellow powder. Total yield of the product was 728.7 g (89%).

B. Preparation of a Compound of Formula (4), Varying $R^1$ and $R^2$

Similarly, following the procedure of Example 5A above, but substituting other compounds of formula (3) for 3-ethyl-5-methyl-1,3-dihydrothiopheno[2,3-b]pyrimidine-2,4-dione, the following compounds of formula (4) are prepared Example 6

Preparation of a Compound of Formula (5')

A. Preparation of a Compound of Formula I in which $R^4$ and $R^5$ are Hydrogen, and $R^6$ is 3-Methoxyphenyl

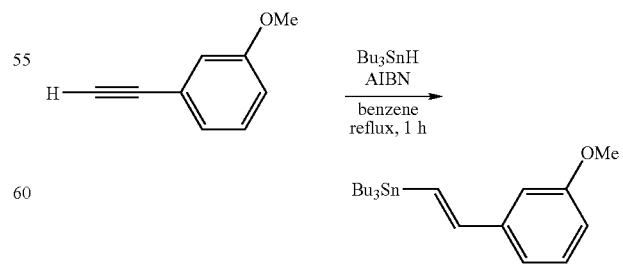

3-Methoxyphenylacetylene (304.0 mg, 2.30 mmol) was placed in a 25 mL flask equipped with a condenser. To the flask was added benzene (3 mL) at room temperature under nitrogen atmosphere to dissolve the starting material. To the mixture were added Bu₃SnH (1.2 mL, 4.60 mmol, 2.0 equiv) and AIBN (2,2'-azobisisobutyronitrile, 75.5 mg, 0.46 mmol, 0.2 equiv). The mixture was heated under reflux condition for 1 hour. After removal of the solvent, the mixture was purified by column-chromatography (SiO₂=80 g, hexane/EtOAc=1:50) to give the desired product (780.3 mg, 2.68 mmol, quant) as a colorless oil.

B. Preparation of a Compound of Formula (5'), Varying $R^6$

Similarly, following the procedure of Example 6A above, but substituting other acetylene compounds for 3-methoxyphenylacetylene, the following compounds of Formula I was prepared:
2-(pyrid-3-yl)vinyltributylstannane.

C. Preparation of Compounds of Formula I Varying $R^1$, $R^3$ and $R^6$

Similarly, following the procedure of Example 6A above, but substituting other acetylene compounds for 3-methoxyphenylacetylene, the following compounds of Formula I are prepared.

Example 7

Preparation of a Compound of Formula I

A. Preparation of a Compound of Formula I in which $R^1$ is Ethyl, $R^2$, $R^4$, and $R^5$ are Hydrogen, $R^3$ is Methyl, and $R^6$ is 2-Methoxyphenyl

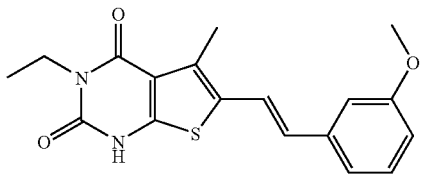

A 3 mL Smith Process Vial was charged with 6-iodo-3-ethylthieno[2,3-b]pyrimidine-2,4-dione (56.7 mg, 0.1688 mmol), 2-(pyrid-3-yl)tributylvinylstannane (122.8 mg, 0.422 mmol, 2.5 equiv) and Pd(Ph₃P)₄ (9.8 mg, 0.00844 mmol, 0.05 equiv) under argon atmosphere. Into the flask were added DMF (2 mL) at room temperature so that concentration of the starting material becomes 0.07 M. The mixture was heated by microwave reactor at 160° C. for 10 min. (Emrys Optimizer microwave, Smith Process Vial and Emrys Optimizer are registered trademarks of Personal chemistry, Inc., Uppsala) The mixture was filtered through Celite (3 g) and the Celite was washed with EtOAc (70 mL). The filtrate was washed with brine (30 mL) and dried with Na₂SO₄. After filtering off the drying agent, the solvent was removed under reduced pressure to give a crude mixture. After a purification using a column-chromatography (SiO₂=80 g, hexane/EtOAc=1:50), obtained material was purified by a recrystallization (CH₂Cl₂/hexane=4 mL/4 mL) afforded the 6-[(1E)-2-(3-methoxyphenyl)vinyl]-3-ethyl-5-methyl-1,3-dihydrothiopheno[2,3-b]pyrimidine-2,4-dione as a light yellow powder.

B. Preparation of a Compound of Formula I, Varying $R^1$, $R^2$, and $R^3$

Similarly, following the procedure of Example 7A above, but optionally substituting other compounds of formula (4) for 6-iodo-3-ethylthieno[2,3-b]pyrimidine-2,4-dione, and optionally substituting other vinylstannane derivatives for 2-(pyrid-3-yl)vinyltributylstannane, the following compounds of Formula I was prepared:
6-[(1E)-2-(pyrid-3-yl)vinyl]-3-ethyl-5-methyl-1,3-dihydrothio-pheno[2,3-b]pyrimidine-2,4-dione.

C. Preparation of Compounds of Formula I Varying $R^1$, $R^3$ and $R^6$

Similarly, following the procedure of Example 7A above, but optionally substituting other compounds of formula (4) for 6-iodo-3-ethylthieno[2,3-b]pyrimidine-2,4-dione, and optionally substituting other vinylstannane derivatives for 2-(pyrid-3-yl)vinyltributylstannane, the following compounds of Formula I are prepared.

Example 8

Preparation of a Compound of Formula I Wherein $R^2$ is Other than Hydrogen

A. Preparation of a Compound of Formula I in which $R^1$ is Ethyl, $R^4$, and $R^5$ are Hydrogen, $R^2$ and $R^3$ are Methyl, and $R^6$ is Phenyl

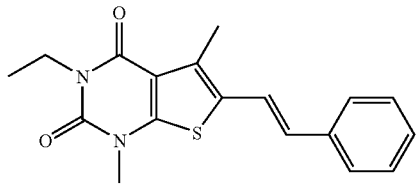

A 10 mL round bottom flask was charged with 3-ethyl-5-methyl-6-(E-2-phenylethenyl}thieno[2,3-b]pyrimidine-2,4-dione. The starting material was dissolved into DMF (0.5 mL) and the solution was treated with i-Pr₂NEt (6.2 mg, 0.048 mmol, 5 equiv) and MeI (4.1 mg, 0.0288 mmol, 3 equiv) at room temperature. The mixture was stirred for 2 hours at the same temperature. To the reaction mixture was added H₂O (30 mL) and the whole was extracted with AcOEt (3×30 mL). Combined organic layers were washed with brine (30 mL) and dried with Na₂SO₄. After removal of the drying agent by filteration, the solvent was removed under reduced pressure. Obtained crude mixture was purified by a column-chromatography (SiO₂=25 g, hexane/EtOAc=1:1) to give the methylated product.

¹H NMR: (400 MHz, DMSO).
1.13 (3H, t, J=7.0 Hz, NCH₂CH₃), 2.56 (3H, s, C (5)Me), 3.47 (3H, s, NMe), 3.91 (2H, q, J=7.0 Hz, NCH₂CH₃), 6.82 (1H, d, J=16.0 Hz, —CH═CH-Ph), 7.26 (1H, bd t, J=7.4 Hz, C (4") H), 7.36 (2H, br t, J=7.4 Hz, C (3") H+C (5") H), 7.50 (1H, d, J=16.0 Hz, —CH═CH-Ph), 7.63 (2H, br d, J=7.4 Hz, C (2") H+C (6") H).
MS (EI): 326 (M⁺+1), 272, 190.

B. Preparation of a Compound of Formula I, Varying $R^1$, $R^2$ and $R^3$

Similarly, following the procedure of Example 8A above, but optionally substituting other compounds of Formula I wherein $R^2$ is hydrogen for 3-ethyl-5-methyl-6-(E-2-phenylethenyl}thieno[2,3-b]pyrimidine-2,4-dione, and optionally substituting other halogenated $R^2$ derivatives for MeI, the following compounds of Formula I were prepared:
6-((1E)-2-phenylvinyl)-1,3-diethyl-5-methyl-1,3-dihydrothiopheno[2,3-b]pyrimidine-2,4-dione;

6-((1E)-2-phenylvinyl)-3-ethyl-1-(2-hydroxyethyl)-5-methyl-1,3-dihydrothiopheno[2,3-b]pyrimidine-2,4-dione;
6-((1E)-2-phenylvinyl)-3-ethyl-1-(3-hydroxypropyl)-5-methyl-1,3-dihydrothiopheno[2,3-b]pyrimidine-2,4-dione; and
6-((1Z)-2-phenylvinyl)-3-ethyl-1-(2-hydroxyethyl)-5-methyl-1,3-dihydrothiopheno[2,3-b]pyrimidine-2,4-dione.

Example 9

Preparation of a Compound of Formula (7)

A. Preparation of a Compound of Formula (7) in which $R^1$ is Ethyl and $R^3$ is Methyl

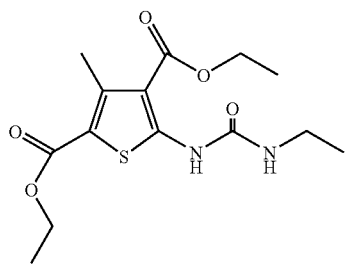

A mixture of propionic acid (0.8 ml, 10 mol), diphenylphosphoryl azide (2.22 ml, 10.3 mmol) and triethylamine (1.39 ml, 10 mmol) in toluene (15 ml) was refluxed for 90 minutes. The mixture was then cooled to below 40° C., and a solution of ethyl 2-amino-5-(ethoxycarbonyl)-4-methylthiophene-3-carboxylate (1.76 g, 6.85 mmol) in toluene (10 ml) was added, the mixture refluxed for 24 hours. The reaction mixture was diluted with brine, and extracted with ethyl acetate. The organic layer was washed with brine and dried over sodium sulfate. Solvent was removed under reduced pressure, and the residue purified by column chromatography, eluting with ethyl acetate/hexane 1:6 to 1:4, to provide ethyl 5-(ethoxycarbonyl)-2-[(ethylamino)carbonylamino]-4-methylthiophene-3-carboxylate. The structure was confirmed by $^1$H NMR and mass spectrometry.

B. Preparation of Other Compounds of Formula (7)

Similarly, following the procedure of Example 9A above, but optionally substituting ethyl 2-amino-5-(ethoxycarbonyl)-4-methylthiophene-3-carboxylate with other compounds of formula (4), and optionally substituting propionic acid with other carboxylic acids of formula $R^1CO_2H$, other compounds of formula (7) are prepared.

Example 10

Preparation of a Compound of Formula (8)

A. Preparation of a Compound of Formula (8) in which $R^1$ is Ethyl and $R^3$ is Methyl

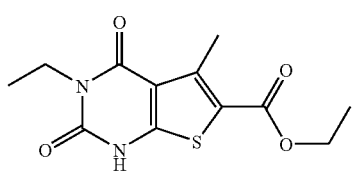

To a solution of ethyl 5-(ethoxycarbonyl)-2-[(ethylamino)carbonylamino]-4-methylthiophene-3-carboxylate (0.93 g, 2.84 mmol) in ethanol (20 ml) was added a solution of sodium ethoxide in ethanol (21% w/w, 2 ml). The mixture was stirred at room temperature overnight, cooled to 0° C., and acidified with 1N hydrochloric acid. Solvent was removed from the mixture under reduced pressure, and to the solid residue was added water, and the resulting solid filtered off, washed with water, and recrystallized from ethanol, to provide ethyl 3-ethyl-5-methyl-2,4-dioxo-1,3-dihydrothiopheno[2,3-b] pyrimidine-6-carboxylate. Mass spectrometry and $^1$H NMR were satisfactory.

B. Preparation of Other Compounds of Formula (8)

Similarly, following the procedure of Example 10A above, but replacing ethyl 5-(ethoxycarbonyl)-2-[(ethylamino)carbonylamino]-4-methylthiophene-3-carboxylate with other compounds of formula (7), other compounds of formula (8) are prepared.

Example 11

Preparation of a Compound of Formula (9)

A. Preparation of a Compound of Formula (9) in which $R^1$ is Ethyl and $R^2$ and $R^3$ are Methyl

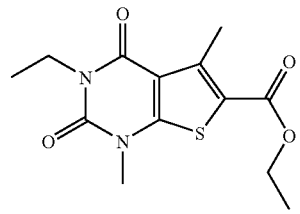

A 100 mL round bottom flask was charged with ethyl 3-ethyl-5-methylthieno[2,3-b]pyrimidine-2,4-dione-6-carboxylate. Into the flask was added DMF (4 mL) at room temperature to dissolve the starting material. To the solution were added i-Pr$_2$NEt (3.0 mL, 18.1 mmol, 5 equiv) and MeI (0.67 mL, 10.86 mmol, 3 equiv) successively at room temperature. The mixture was stirred for 1 hour at same temperature. After the reaction went to completion, to the suspension were added H$_2$O (30 mL) and AcOEt (30 mL). However, the precipitates stayed in the biphasic layers and did not dissolve. Hence, this suspension was filtered through glass filter. The residue on the glass filter was washed with AcOEt (10 mL) to give the first crop which is ethyl 3-ethyl-1,5-dimethylthieno [2,3-b]pyrimidine-2,4-dione-6-carboxylate. The filtrate was extracted with AcOEt (2×10 mL). The combined organic layers were washed with brine (30 mL) and dried with Na$_2$SO$_4$. The solvent was removed under reduced pressure to give a crude mixture. Purification of this crude material by recrystallization from AcOEt (4 mL) afforded the second crop.

B. Preparation of Other Compounds of Formula (9)

Similarly, following the procedure of Example 11A above, but replacing ethyl 3-ethyl-5-methylthieno[2,3-b]pyrimidine-2,4-dione-6-carboxylate with other compounds of formula (8), other compounds of formula (9) are prepared.

Example 12

Preparation of a Compound of Formula (10)

A. Preparation of a Compound of Formula (10) in which $R^1$ is Ethyl and $R^2$ and $R^3$ are Methyl

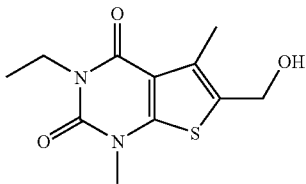

A 100 mL round bottom flask equipped with a condenser was charged ethyl 3-ethyl-1,5-dimethyl-2,4-dioxo-1,3-dihydrothiopheno[2,3-b]pyrimidine-6-carboxylate. Into the flask was added THF (10 mL) at room temperature to suspend the starting material. To the suspension were added $LiBH_4$ (629.2 mg, 28.89 mmol, 9 equiv) at room temperature and the mixture was heated under reflux conditions for 2 hours. After the reaction went to completion, to the suspension were added $H_2O$ (30 mL) and MeOH (20 mL) at 0° C. The whole was extracted with AcOEt (3×30 mL). The combined organic layers were washed with brine (30 mL) and dried with $Na_2SO_4$. The solvent was removed under reduced pressure to give a colorless crude product. Purification of this crude material by recrystallization from AcOEt/hexane (1:1, 18 mL) afforded colorless needles as the first crop. The mother liquid was concentrated and further purified by column-chromatography ($SiO_2$=25 g, hexane/EtOAc=1:1) to give a second crop of the desired product. Mass spectrometry and $^1H$ NMR were satisfactory.

B. Preparation of Other Compounds of Formula (10)

Similarly, following the procedure of Example 12A above, but replacing ethyl 3-ethyl-1,5-dimethyl-2,4-dioxo-1,3-dihydrothiopheno[2,3-b]pyrimidine-6-carboxylate with other compounds of formula (9), other compounds of formula (10) are prepared.

Example 13

Preparation of a Compound of Formula (11)

A. Preparation of a Compound of Formula (11) in which $R^1$ is Ethyl and $R^2$ and $R^3$ are Methyl

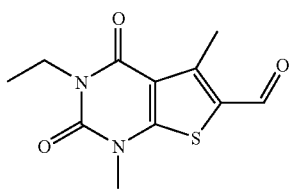

A 100 mL round bottom flask equipped with a condenser was charged with 3-ethyl-1,5-dimethyl-6-hydroxymethylthieno[2,3-b]pyrimidine-2,4-dione. Into the flask were added $MnO_2$ (1.77 g, 20.32 mmol, 8 equiv) and $CHCl_3$ (10 mL) at room temperature. The suspension was heated under reflux conditions for 1 hour. After the reaction went to completion, to the suspension was added MeOH (30 mL) at room temperature. The oxidizer was filtered off through glass filter using Celite (3 g) and AcOEt (70 mL). The solvent was removed from the filtrate and AcOEt/hexane (1:1) (18 mL) was added to the residue to give the first crop (yellow powder, 540.9 mg). The mother liquid was concentrated and further purified by recrystallization from AcOEt (3 mL) to give the second crop. Obtained mother liquid was concentrated and purified by a column-chromatography ($SiO_2$=25 g, hexane/EtOAc=1:1) to give the third crop.

B. Preparation of Other Compounds of Formula (11)

Similarly, following the procedure of Example 13A above, but replacing 3-ethyl-1,5-dimethyl-6-hydroxymethylthieno[2,3-b]pyrimidine-2,4-dione with other compounds of formula (10), other compounds of formula (11) are prepared.

Example 14

Preparation of a Compound of Formula (12)

A. Preparation of a Compound of Formula I in which $R^4$ and $R^5$ are Hydrogen, and $R^6$ is 3,4-Dimethoxyphenyl

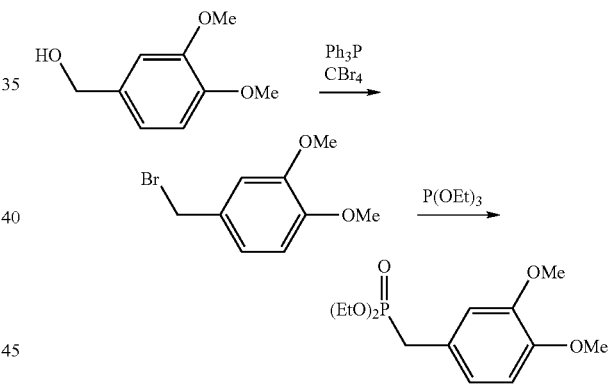

A 1 L round bottom flask equipped with $N_2$ inlet was charged with $CBr_4$ (5.48 g, 16.53 mmol, 1 equiv) and $CHCl_3$ (30 mL). To the solution was added $PPh_3$ (8.67 g, 33.06 mmol, 2 equiv) under nitrogen atmosphere at room temperature. After stirring for 30 min at the same temperature, 3,5-dimethoxybenzyl alcohol (2.78 g, 16.53 mmol) was added. The reaction mixture was stirred for 1 hour again at the same temperature. To the mixture was added hexane (600 mL). After stirring for 14 hours, sticky brownish yellow material was sticking on the surface of the flask. The supernatant was decanted and filtered through a glass filter. And then the solvent was removed from the filtrate under reduced pressure to give a crude benzyl bromide.

Obtained crude product was immediately subjected to the subsequent reaction conditions. To the crude benzyl bromide was added $P(OEt)_3$ (5.49 g, 33.06 mmol, 2 equiv) at room temperature. The mixture was heated under reflux conditions for 1 hour. After cooling down to ambient temperature, the mixture was directly loaded onto a column-chromatography (SiO$_2$=80 g, hexane/EtOAc=1:1 to AcOEt to 20% MeOH/AcOEt) to give the phosphonate.

Example 15

Preparation of a Compound of Formula I

A. Preparation of a Compound of Formula I in which R$^1$ is Ethyl, R$^2$ and R$^3$ are Methyl, R$^4$ and R$^5$ are Hydrogen, and R$^6$ is 3,4-Dimethoxyphenyl

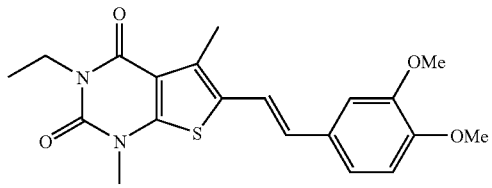

A 250 mL round bottom flask equipped with N$_2$ inlet was charged with 3-ethyl-1,5-dimethylthieno[2,3-b]pyrimidine-2,4-dione-6-carboxyaldehyde (562.9 mg, 2.231 mmol), and diethyl (3,4-dimethoxyphenyl)methylphosphonate (965.7 mg, 3.35 mmol, 1.5 equiv). These starting materials were dissolved into THF (7 mL). To the solution was added t-BuOK (500.7 mg, 4.46 mmol, 2 equiv) under nitrogen atmosphere at room temperature. After stirring for 2 hours at the same temperature, further 1 equiv. of t-BuOK (250.3 mg, 2.23 mmol) was added. The reaction mixture was stirred for another 1 hour at room temperature. After complete disappearance of the aldehyde, H$_2$O (20 mL) and AcOEt (30 mL) were added to the mixture. Resulting biphasic suspension was filtered through glass filter to obtain the first crop of crude product as a light brown powder. The crude product was recrystallized from DMF/benzene (2 mL+10 mL) to give pure desired product as a light brown powder (168.2 mg). All the mother liquid was combined and extracted with AcOEt (3×30 mL). Combined organic layers were washed with brine (30 mL) and dried with Na$_2$SO$_4$. The solvent was removed under reduced pressure to give another crude product. This was purified by a column-chromatography (SiO$_2$=80 g, hexane/EtOAc=1:1) and a recrystallization from AcOEt/hexane (1:1, 10 mL) to give the desired product.

$^1$H NMR: (400 MHz, DMSO).

1.24 (3H, t, J=6.7 Hz, NCH$_2$CH$_3$), 2.55 (3H, s, C (5)Me), 3.46 (3H, s, NMe), 3.76 (3H, s, OMe), 3.82 (3H, s, OMe), 3.90 (2H, q, J=6.7 Hz, NCH$_2$CH$_3$), 6.74 (1H, d, J=16.0 Hz, —CH=CH—C$_6$H$_3$(OMe)$_2$), 6.92 (1H, d, J=8.2 Hz, C (5") H), 7.09 (2H, dd, J=8.2, 1.2 Hz, C (6") H), 7.26 (1H, d, J=1.2 Hz, C (2") H), 7.63 (2H, br d, J=7.4 Hz, —CH=CH—C$_6$H$_3$(OMe)$_2$).

B. Preparation of Other Compounds of Formula I with Varying R$^6$

Similarly, following the procedure of Example 15A above, but replacing 3-ethyl-1,5-dimethylthieno[2,3-b]pyrimidine-2,4-dione-6-carboxyaldehyde with other compounds of formula (11) and/or replacing diethyl (3,4-dimethoxyphenyl) methylphosphonate with other compounds of formula (12), the following other compounds of Formula I are prepared.

Example 16

Preparation of Compounds of Formula I

A. Preparation of a Compound of Formula (3) wherein R$^1$ is prop-2-ynyl, R$^3$ is methyl Following the procedure of Example 2A, but substituting ethyl 4-methyl-2-[(prop-2-ynylamino)carbonylamino]thiophene-3-carboxylate for ethyl 4-methyl-2-[(methylamino)carbonylamino]thiophene-3-carboxylate, 3-ethyl-5-prop-2-ynyl-1,3-dihydrothiopheno[2,3-b]pyrimidine-2,4-dione was prepared.

B. Alkylation of a Compound of Formula (3) to form a compound wherein R$^1$ is prop-2-ynyl, R$^3$ is methyl, and R$^2$ is methyl To a solution of 3-ethyl-5-prop-2-ynyl-1,3-dihydrothiopheno[2,3-b]pyrimidine-2,4-dione in DMF, potassium carbonate (2 eq.) was added followed by methyl iodide (2 eq.) and stirred at room temperature for 4 hours. After completion of the starting material, the solvent was distilled off and the residue was treated with water. The precipitate was filtered and washed with water and dried. An NMR was consistent with the structure and the compound, 1,5 dimethyl-3-prop-2-ynyl-1,3-dihydrothiophene[2,3-b]pyrimidine-2,4-dione, was used for the next step.

C. Iodination of the Compound formed in B wherein R$^1$ is prop-2-ynyl, R$^3$ is methyl, and R$^2$ is methyl To a solution of the compound formed in B in chloroform at 0° C., N-iodosuccinamide (1.2 eq.) was added slowly portion-wise over a period of 30 minutes and then stirred for 2 hours. The precipitate was filtered, washed with chloroform, and dried. This product was used in step D.

D. Preparation of a Compound of Formula I in which R$^1$ is prop-2-ynyl, R$^2$ and R$^3$ are methyl, R$^4$ and R$^5$ are hydrogen, and R$^6$ is phenyl Following the procedure of Example 4A above, but optionally substituting other compounds for 6-bromo-3-ethylthieno[2,3-b]pyrimidine-2,4-dione, and optionally substituting other boronic acid derivatives for 2-phenylethenylboronic acid, the following compound of Formula I was prepared: 6-((1E)-2-phenylvinyl)-1,5-dimethyl-3-prop-2-ynyl-1,3-dihydrothiopheno[2,3-d]pyrimidine-2,4-dione.

E. Preparation of Other Compounds of Formula I

Similarly, following the procedures of Example 16A-D above, but replacing ethyl 4-methyl-2-[(prop-2-ynylamino)carbonylamino]thiophene-3-carboxylate with other compounds of formula (2), the following compound of Formula I was prepared:
6-[(1E)-2-(3,4-dimethoxyphenyl)vinyl]-3-ethyl-5-methyl-1-[(phenylmethoxy)methyl]-1,3-dihydrothiopheno[2,3-d]pyrimidine-2,4-dione.

Example 17

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Example 18

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 19

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Example 20

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 21

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Example 22

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 23

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 24

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 25

A subcutaneous formulation may be prepared as follows:

| Ingredient | Quantity |
| --- | --- |
| Active Ingredient | 5.0 mg |
| Corn Oil | 1.0 mL |

Example 26

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Example 27

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Example 28

Sustained Release Composition

| Ingredient | Weight Range (%) | Preferred Range (%) | Most Preferred |
| --- | --- | --- | --- |
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base that is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, for example sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methyl-butyl methacrylate copolymers— Eudragit® E—Röhm. Pharma), and the like. These film-forming agents may optionally contain colorants, plasticizers, and other supplemental ingredients.

The compressed tablets for example have a hardness sufficient to withstand 8 Kp compression. The tablet size will depend primarily upon the amount of compound in the tablet. The tablets will include from 300 to 1100 mg of compound free base. For example, the tablets will include amounts of compound free base ranging from 400-600 mg, 650-850 mg, and 900-1100 mg.

In order to influence the dissolution rate, the time during which the compound containing powder is wet mixed is controlled. For example the total powder mix time, i.e. the time during which the powder is exposed to sodium hydroxide solution, will range from 1 to 10 minutes and for example from 2 to 5 minutes. Following granulation, the particles are removed from the granulator and placed in a fluid bed dryer for drying at about 60° C.

Example 29

Determination of $A_{2A}$ Antagonist Activity

Reagents:

A tritiated adenosine $A_{2A}$ antagonist, 3-(3-hydroxypropyl)-7-methyl-8-(m-methoxystyryl)-1-propargylxanthine, (3H-MSX-2, specific activity: 80 Ci/mmol), was purchased from American Radiolabeled Chemicals, Inc (St. Louis, Mo.). A tritiated adenosine $A_1$ antagonist, 1,3-Dipropyl-8-cyclopentylxanthine ([$^3$H]DPCPX, specific activity: 120 Ci/mmol) was purchased from Perkin Elmer (Boston, Mass.). A tritiated adenosine $A_{2B}$ antagonist, 4-(2-[7-amino-2-(2-furyl) [1,2,4]triazolo[2,3-a][1,3,5]triazin-5-ylamino]ethyl) phenol ([$^3$H]ZM241385 specific activity: 27.4 Ci/mmol) was purchased from American Radiolabeled Chemicals, Inc (St. Louis, Mo.). Adenosine Deaminase (ADA) was purchased from Roche Molecular Biochemicals (Nutley, N.J.). GTP was purchased from Sigma. Concentrated stock solution (10 mM) of compounds was dissolved in dimethylsulfoxide (DMSO), stored at −20° C., and diluted in Tris-EDTA buffer (50 mM Tris and 1 mM EDTA, 10 mM $MgCl_2$, pH 7.4) for use in experiments. The final content of dimethylsulfoxide in Tris-EDTA buffer during experiments was not more than 1%. Male Sprague Dawley rats, weighted 250-400 g, 8-10 weeks old, were purchased from Charles River Labs (Wilmington, Mass.).

Cell Culture

HEK293 (Human Embryonic Kidney 293) cells stably expressing human $A_{2A}$ adenosine receptor or human $A_{2B}$ adenosine receptor were maintained in DMEM supplemented with 10% fetal bovine serum, 2 mM L-glutamine, 100 IU/ml penicillin, 50 μg/ml streptomycin and 2 μg/ml puromycin. CHO (Chinese Hamster Ovary) cells stably expressing human $A_1$ adenosine receptor or human $A_3$ adenosine receptor were maintained in F12K medium supplemented with 10% fetal bovine serum, 2 mM L-glutamine, 100 IU penicillin, 50 μg/ml streptomycin and 8 μg/ml puromycin. PC12 (rat pheochromocytoma) cells were cultured in F12K medium supplemented with 10% horse serum and 2.5% fetal bovine serum, 2 mM L-glutamine, 100 IU/ml penicillin, and 50 μg/ml streptomycin. All cells were maintained at 37° C. in a humidified 5% $CO_2$/95% air incubator and recultivated 2 times per week.

Membrane Preparations

Cultured cells in 150 $mm^2$ dishes were washed once with PBS, detached by scrapping, collected with buffer A (10 mM HEPES, 10 mM EDTA, pH 7.4) containing protease inhibitor cocktail. Cells were then homogenized by a handheld homogenizer at a speed of 4.5 for 1 min. The homogenate was centrifuged by a Beckman ultracentrifuge at a speed of 29,000×g for 15 min. The pellets were resuspended in buffer HE (10 mM HEPES, 1 mM EDTA, pH 7.4, with protease inhibitor cocktail), centrifuged again at 29,000×g for 15 min. The crude membrane was resuspended using buffer HE, and protein concentration was measured by the method of Lowery with BSA as standard. Similar procedures were used for membrane preparation for fresh rat tissues. All experimental procedures were done at 4° C. Membranes were aliquot and kept at −80° C.

Radioligand Binding Assays:

The binding assays utilized 15 ug of $A_{2A}$ membrane (human recombinant $A_{2A}$ membrane, rat striatal membrane, or PC 12 cell membrane) that had been treated with adenosine deaminase and 50 mM Tris-EDTA buffer (pH=7.4) followed by mixing 2 μL of serially diluted DMSO stock solution of the compounds of this invention at concentrations ranging from 10 μM to 0.1 nM or the control received 2 μL of DMSO alone, then the tritiated antagonist 3-(3-hydroxypropyl)-7-methyl-8-(m-methoxystyryl)-1-propargylxanthine (3H-MSX-2) in Tris-EDTA buffer (50 mM Tris, 1 mM EDTA, 10 mM $MgCl_2$, pH of 7.4) was added to achieve a final concentration of 2 nM. After incubation at 23° C. for 2 hours, the solutions were filtered using a membrane harvester with multiple washing of the membranes (3×). The filter plates were counted in scintillation cocktail affording the amount of displacement $^3$H-MSX-2 by the competitive binding compositions of this invention. Radioligand binding data was analyzed using GraphPad Prism version 4.0 (San Diego, Calif.). When appropriate, the significance of differences among 3 or more individual mean values was determined by one-way ANOVA followed by Student-Newman-Keuls test. A P value less than 0.05 was considered to indicate a statistically significant difference.

Using the above competitive binding assays, Ki($A_{2A}$) data was generated for the compounds of the invention. Data for a number of representative compounds is presented in Table 1 below.

| EXAMPLE No. | NAME | $K_i(A_{2A})$ nM |
|---|---|---|
| I. | 6-[(1E)-2-(3,4-dimethoxyphenyl)vinyl]-3-ethyl-1,5-dimethyl-1,3-dihydrothiopheno[2,3-d]pyrimidine-2,4-dione | 220 |
| II. | 6-[(1E)-2-(3,4-dimethoxyphenyl)vinyl]-3-ethyl-5-methyl-1-[(phenylmethoxy)methyl]-1,3-dihydrothiophene[2,3-d]pyrimidine-2,4-dione | 866 |
| III. | 6-((1E)-2-phenylvinyl)-3-ethyl-5-methyl-1,3-dihydrothiopheno[2,3-d]pyrimidine-2,4-dione | 171 |
| IV. | 6-[(1E)-2-(4-fluorophenyl)vinyl]-3-ethyl-5-methyl-1,3-dihydrothiopheno[2,3-d]pyrimidine-2,4-dione | 189 |
| V. | 6-((1E)-2-phenylvinyl)-1,5-dimethyl-3-prop-2-ynyl-1,3-dihydrothiopheno[2,3-d]pyrimidine-2,4-dione | 390 |
| VI. | 6-[(1E)-2-(3-fluorophenyl)vinyl]-3-ethyl-5-methyl-1,3-dihydrothiopheno[2,3-d]pyrimidine-2,4-dione | 242 |
| VII. | 6-[(1E)-2-(4-chlorophenyl)vinyl]-3-ethyl-5-methyl-1,3-dihydrothiopheno[2,3-d]pyrimidine-2,4-dione | 320 |
| VIII. | 6-[(1E)-2-(4-phenylphenyl)vinyl]-3-ethyl-5-methyl-1,3-dihydrothiopheno[2,3-d]pyrimidine-2,4-dione | 776 |
| IX. | 6-{(1E)-2-[4-(trifluoromethyl)phenyl]vinyl}-3-ethyl-5-methyl-1,3-dihydrothiopheno[2,3-d]pyrimidine-2,4-dione | 674 |
| X. | 6-[(1E)-2-(3,4-dimethoxyphenyl)vinyl]-3-ethyl-5-methyl-1,3-dihydrothiopheno[2,3-d]pyrimidine-2,4-dione | 75 |
| XI. | 6-[(1E)-2-(3,4-dimethoxyphenyl)vinyl]-5-methyl-3-(2-methylpropyl)-1,3-dihydrothiopheno[2,3-d]pyrimidine-2,4-dione | 277 |

-continued

| EXAMPLE No. | NAME | $K_i(A_{2A})$ nM |
|---|---|---|
| XII. | 6-((1E)-2-(3-pyridyl)vinyl)-3-ethyl-5-methyl-1,3-dihydrothiopheno[2,3-d]pyrimidine-2,4-dione | 33 |
| XIII. | 6-[(1E)-2-(4-methylphenyl)vinyl]-3-ethyl-5-methyl-1,3-dihydrothiopheno[2,3-d]pyrimidine-2,4-dione | 182 |
| XIV. | 6-[(1E)-2-(4-methoxyphenyl)vinyl]-3-ethyl-5-methyl-1,3-dihydrothiopheno[2,3-d]pyrimidine-2,4-dione | 119 |
| XV. | 6-[(1E)-2-(2-fluorophenyl)vinyl]-3-ethyl-5-methyl-1,3-dihydrothiopheno[2,3-d]pyrimidine-2,4-dione | 170 |
| XVI. | 6-[(1E)-2-(3-methoxyphenyl)vinyl]-3-ethyl-5-methyl-1,3-dihydrothiopheno[2,3-d]pyrimidine-2,4-dione | 104 |
| XVII. | 6-[(1E)-2-(2-methoxyphenyl)vinyl]-3-ethyl-5-methyl-1,3-dihydrothiopheno[2,3-d]pyrimidine-2,4-dione | 38 |
| XVIII. | 6-[(1E)-2-(3,5-dimethoxyphenyl)vinyl]-3-ethyl-5-methyl-1,3-dihydrothiopheno[2,3-d]pyrimidine-2,4-dione | 96 | cAMP Assay

The ability of the putative $A_{2A}$ antagonist to inhibit cAMP accumulation was determined as follows. HEK293-$A_{2A}$ cells and PC12 cells were seeded on 150×25 mm tissue culture dishes and grown 36-72 h to reach ~80% confluence. Cells were then washed once with PBS and detached with PBS containing 2 mM EDTA. Cells were pelleted at a speed of 1000 rpm and resuspended in Opti-MEM I. ADA (1 U/ml) was added to eliminate adenosine. Cells were loaded into 96-well plates (~6500 cells/well) and incubated with the $A_{2A}$ agonist CGS21680 in the absence or presence of the putative adenosine $A_{2A}$ receptor antagonists (pretreated for 5 min) for 30 min at 37° C. The cAMP production was then measured using a DiscoveRx kit according to the manufacturer's instructions.

Example 30

Evaluation of Anti-Parkinsonian Activity In Vivo Haloperidol-Induced Catalepsy in the Rat This method assesses the ability of an animal to respond to an externally imposed posture after receiving the neuroleptic dopamine D2 antagonist haloperidol. Drugs which are effective in treating Parkinson's disease, such as L-DOPA, block haloperidol-induced catalepsy (Mandhane, S. N.; Chopde, C. T.; Ghosh, A. K. (1997). Adenosine $A_{2A}$ receptors modulate haloperidol-induced catalepsy in rats.

The compounds of the invention are prepared in injectable form and diluted to a final concentration using physiological saline. 3,7-Dimethyl-1-propargylxanthine (DMPX) (0.3 mg/kg) is dissolved in saline. All drugs are administered in a volume of 2 ml/kg. Animals receive three injections: (1) vehicle or compound p.o. 6 hours prior to testing, (2) haloperidol (0.2 mg/kg) i.p. 2.5 hours prior to testing, and (3) vehicle or DMPX (3 mg/kg) 30 minutes prior to testing.

The test procedure is as follows:
Step I The rat is taken out of the home cage and placed on a table. If the rat failed to move when touched gently on the back or pushed, a score of 0.5 is assigned.
Step II The front paws of the rat are placed alternately on a 3 cm high wooden block. If the rat fails to correct this posture within 15 seconds, a score of 0.5 for each paw is added to the score of Step I.
Step III The front paws of the rat are placed alternately on a 9 cm high wooden block. If the rat fails to correct the posture within 15 seconds, a score is added to the scores of Step I and II. Thus, for any animal, the highest score obtainable is 3.5 (cut-off score) reflecting total catalepsy.

Data from the experiment are analysed using Kruskal-Wallis ANOVA followed by Mann-Whitney U test when appropriate, and are expressed as means+/− standard error of the mean*p<0.05 versus vehicle control.

MPTP Lesion Model

Mice (C57/BL Harlan) receive a unilateral intrastriatal injection of the test compound, vehicle control, and positive control, in a volume of 1.0. mu.l (15 mice per group). 30 min. after administration of the test compound all mice are systemically administered MPTP (N-methyl-4-phenyl-1,2,5,6-tetrahydropyridine) (25 mg/kg s.c), and this MPTP treatment is repeated 24 hours later. At suitable time points the spontaneous locomotor activity of the animals, as measured in automated activity monitors, is compared with control animals.

Animals are sacrificed 14 days after the second MPTP injection and striatal tissue is dissected out for HPLC analysis of dopamine and its metabolites, 3,4-dihydroxyphenylacetic acid and homovanillic acid. Reverse-phase HPLC in conjunction with electrochemical detection (Antec Decade detector, glossy carbon cell, set to +0.65 V versus a Ag/AgCl reference) is employed. The HPLC mobile phase consisted of 0.15 M $NaH_2PO_4$, 0.1 mM EDTA, 0.55 mM octyl sulphate, 16% methanol (pH 3.6, adjusted with orthophosphoric acid).

The effects of test compounds on MPTP-induced mesencephalic damage is demonstrated by comparison with dopamine, 3,4-dihydroxyphenylacetic acid and homovanillic acid levels in caudate tissue taken ipsilateral and contralateral to the test compound injection. The influence of test compounds on MPTP-induced effects on locomotion and catecholamine and metabolite tissue levels is assessed by repeated measures analysis of variance (ANOVA) with appropriate tests.

Example 31

Evaluation of Treatment of Alcohol Abuse In Vivo in the Rat

Male Long Evans rats (Harlan, Indianapolis, Ind.), weighing approximately 250 g, are individually housed with food and water available ad libitum, and maintained on a 12 hour light/dark cycle. Ethanol dilution (10% v/v) for self-administration is prepared using 95% ethyl alcohol and tap water. Sucrose solution (10% w/v) is prepared using tap water. The test compound is dissolved in warm saline, and administered in a 1 ml/kg volume. Ethanol operant self-administration is carried out in standard operant chambers (Med Associates, Georgia, Vt.) housed in sound-attenuated cubicles. Each chamber (33×30.5×33 cm) contains two retractable levers against the right wall, 7 cm from the floor and 1 cm from the right or left edge of the right wall, respectively. One recessed dish positioned at 2.5 cm above floor level and 6 cm from the levers towards the center of the chamber is the reinforcer receptacle. Fluid (0.1 ml) is delivered from 10 syringe pumps upon activation of 1 of the 2 retractable response levers. A 3 second tone is activated upon lever pressing. Pressing the inactive lever resulted in no visual/auditory cue or reinforcement delivery, except during sucrose overnight sessions. The beginning of a training session is signaled by the onset of the house light located in the center of the wall facing the levers, at 27.2 cm above the floor. A computer-controlled stimulus and fluid delivery and recorded operant responses.

Before the beginning of the ethanol operant self-administration, rats are exposed to a 10% ethanol solution as the only liquid source in their home cages for 4 days. For the next 14 days, animals are allowed free choice between 10% ethanol solution in tap water or tap water from graded glass tubes. At the end of this 14-day period, operant self-administration is initiated according to the sucrose fading technique (Samson, 1986) with minor modifications. Rats are restricted to 30 minutes of water per day for 2 consecutive days. On the night of the second day of water restriction, rats are placed in the operant chambers for a 12-15 hours overnight session on an FR1 schedule (1 reinforcement of 0.1 ml per lever press) with 10% sucrose as a reinforcer and both levers active. The next day, rats begin the operant self-administration training. Animals are kept on water restriction for the next 4-5 days, during which they receive one 45 minute session per day on an FR1 schedule with 10% ethanol solution as a reinforcer and one active lever. They are then given free water in their home cages for the remainder of the experiment and are trained for 2-3 more of the above described sessions. The next day, sessions are shortened to 30 minutes and the ratio of responding was increased to an FR3 schedule. Ethanol is added to the sweet solution (10% sucrose/10% ethanol), and rats receive 3-4 sessions of this solution, followed by at least 20 sessions with 10% ethanol only. A minimum average of 0.3 g/kg ethanol consumption in 8 sessions prior to the beginning of any drug treatment is required.

We claim:
1. A compound of Formula I:

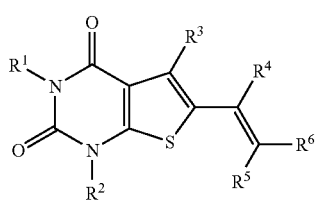

Formula I wherein
$R^1$ is hydrogen, optionally substituted $C_{1-6}$ alkyl, optionally substituted $C_{2-10}$ alkenyl, or optionally substituted $C_{2-6}$ alkynyl;
$R^2$ is hydrogen, optionally substituted $C_{1-4}$ alkyl, —X—O—P(O)(OR)$_2$, or —X—O—R$^7$, in which X is $C_{1-4}$ alkylene, R is hydrogen or $C_{1-6}$ alkyl, and $R^7$ is $C_{1-6}$ alkyl;

$R^3$ is hydrogen, optionally substituted $C_{1-4}$ alkyl, or a 5 or 6 membered optionally substituted monocyclic heterocycle containing 1, 2, 3, or 4 heteroatoms independently selected from oxygen, sulfur and nitrogen;
$R^4$ and $R^5$ are independently methyl or hydrogen; and
$R^6$ is optionally substituted phenyl, optionally substituted heteroaryl, optionally substituted heterocycle, or optionally substituted cycloalkyl,
or a pharmaceutically acceptable salt thereof.
2. The compound of claim 1, wherein $R^2$ is hydrogen.
3. The compound of claim 2, wherein $R^1$ is optionally substituted $C_{1-6}$ alkyl.
4. The compound of claim 3, wherein $R^3$ is optionally substituted $C_{1-4}$ alkyl.
5. The compound of claim 4, wherein $R^6$ is optionally substituted phenyl or optionally substituted heteroaryl.
6. The compound of claim 5, selected from the group consisting of:
  6-[(1E)-2-(4-fluorophenyl)vinyl]-3-ethyl-5-methyl-1,3-dihydrothiopheno[2,3-d]pyrimidine-2,4-dione;
  6-[(1E)-2-(3-fluorophenyl)vinyl]-3-ethyl-5-methyl-1,3-dihydrothiopheno[2,3-d]pyrimidine-2,4-dione;
  6-[(1E)-2-(4-chlorophenyl)vinyl]-3-ethyl-5-methyl-1,3-dihydrothiopheno[2,3-d]pyrimidine-2,4-dione;
  6-[(1E)-2-(4-phenylphenyl)vinyl]-3-ethyl-5-methyl-1,3-dihydrothiopheno[2,3-d]pyrimidine-2,4-dione;
  6-{(1E)-2-[4-(trifluoromethyl)phenyl]vinyl}-3-ethyl-5-methyl-1,3-dihydrothiopheno[2,3-d]pyrimidine-2,4-dione;
  6-[(1E)-2-(3,4-dimethoxyphenyl)vinyl]-3-ethyl-5-methyl-1,3-dihydrothiopheno[2,3-d]pyrimidine-2,4-dione;
  6-((1E)-2-phenylvinyl)-5-methyl-3-(2-methylpropyl)-1,3-dihydrothiopheno[2,3-d]pyrimidine-2,4-dione;
  6-[(1E)-2-(3,4-dimethoxyphenyl)vinyl]-5-methyl-3-(2-methylpropyl)-1,3-dihydrothiopheno[2,3-d]pyrimidine-2,4-dione;
  6-((1E)-2-(3-pyridyl)vinyl)-3-ethyl-5-methyl-1,3-dihydrothiopheno[2,3-d]pyrimidine-2,4-dione;
  6-[(1E)-2-(4-methylphenyl)vinyl]-3-ethyl-5-methyl-1,3-dihydrothiopheno[2,3-d]pyrimidine-2,4-dione;
  6-[(1E)-2-(4-methoxyphenyl)vinyl]-3-ethyl-5-methyl-1,3-dihydrothiopheno[2,3-d]pyrimidine-2,4-dione;
  6-[(1E)-2-(2-fluorophenyl)vinyl]-3-ethyl-5-methyl-1,3-dihydrothiopheno[2,3-d]pyrimidine-2,4-dione;
  6-[(1E)-2-(3-methoxyphenyl)vinyl]-3-ethyl-5-methyl-1,3-dihydrothiopheno[2,3-d]pyrimidine-2,4-dione;
  6-[(1E)-2-(2-methoxyphenyl)vinyl]-3-ethyl-5-methyl-1,3-dihydrothiopheno[2,3-d]pyrimidine-2,4-dione; and
  6-[(1E)-2-(3,5-dimethoxyphenyl)vinyl]-3-ethyl-5-methyl-1,3-dihydrothiopheno[2,3-d]pyrimidine-2,4-dione.
7. The compound of claim 1, wherein $R^2$ is optionally substituted $C_{1-4}$ alkyl, —X—O—P(O)(OR)$_2$ or —X—O—R$^7$ in which X is $C_{1-4}$ alkylene, R is hydrogen or $C_{1-6}$ alkyl and $R^7$ is $C_{1-6}$ alkyl.
8. The compound of claim 7, wherein $R^2$ is optionally substituted $C_{1-4}$ alkyl.
9. The compound of claim 8, wherein $R^1$ is optionally substituted $C_{1-6}$ alkyl or optionally substituted $C_{2-6}$ alkynyl.
10. The compound of claim 9, wherein $R^3$ is optionally substituted $C_{1-4}$ alkyl.
11. The compound of claim 10, wherein $R^6$ is optionally substituted phenyl.

12. The compound of claim 11, selected from the group consisting of:
- 6-[(1E)-2-(3,4-dimethoxyphenyl)vinyl]-3-ethyl-1,5-dimethyl-1,3-dihydrothiopheno[2,3-d]pyrimidine-2,4-dione;
- 6-[(1E)-2-(3,4-dimethoxyphenyl)vinyl]-3-ethyl-5-methyl-1-[(phenylmethoxy)methyl]-1,3-dihydrothiopheno[2,3-d]pyrimidine-2,4-dione;
- 6-((1E)-2-phenylvinyl)-1,5-dimethyl-3-prop-2-ynyl-1,3-dihydrothiopheno[2,3-d]pyrimidine-2,4-dione;
- 6-((1E)-2-phenylvinyl)-3-ethyl-1,5-dimethyl-1,3-dihydrothiopheno[2,3-d]pyrimidine-2,4-dione;
- 6-((1E)-2-phenylvinyl)-1,3-diethyl-5-methyl-1,3-dihydrothiopheno[2,3-d]pyrimidine-2,4-dione;
- 6-((1E)-2-phenylvinyl)-3-ethyl-1-(2-hydroxyethyl)-5-methyl-1,3-dihydrothiopheno[2,3-d]pyrimidine-2,4-dione;
- 6-((1E)-2-phenylvinyl)-3-ethyl-1-(3-hydroxypropyl)-5-methyl-1,3-dihydrothiopheno[2,3-d]pyrimidine-2,4-dione; and
- 6-((1Z)-2-phenylvinyl)-3-ethyl-1-(2-hydroxyethyl)-5-methyl-1,3-dihydrothiopheno[2,3-d]pyrimidine-2,4-dione.

13. A pharmaceutical composition comprising a therapeutically effective amount of the compound of claim 1 or a pharmaceutically acceptable salt thereof.

* * * * *